(12) United States Patent
Strother et al.

(10) Patent No.: US 11,583,680 B2
(45) Date of Patent: Feb. 21, 2023

(54) DEEP BRAIN STIMULATOR AND METHOD OF USE

(71) Applicant: Deep Brain Innovations LLC, Cleveland, OH (US)

(72) Inventors: Robert Strother, Willoughby Hills, OH (US); Stuart Rubin, Orange Village, OH (US); Jonathan Sakai, Fairview Park, OH (US)

(73) Assignee: Deep Brain Innovations LLC, Cleveland, OH (US)

( * ) Notice: Subject to any disclaimer, the term of this patent is extended or adjusted under 35 U.S.C. 154(b) by 0 days.

(21) Appl. No.: 14/284,928

(22) Filed: May 22, 2014

(65) Prior Publication Data
US 2014/0350635 A1 Nov. 27, 2014

Related U.S. Application Data

(60) Provisional application No. 61/826,361, filed on May 22, 2013, provisional application No. 61/826,384, (Continued)

(51) Int. Cl.
*A61N 1/36* (2006.01)
*A61N 1/375* (2006.01)
(Continued)

(52) U.S. Cl.
CPC ..... *A61N 1/36178* (2013.01); *A61N 1/36067* (2013.01); *A61N 1/36082* (2013.01);
(Continued)

(58) Field of Classification Search
CPC ............ A61N 1/36178; A61N 1/36067; A61N 1/36082; A61N 1/3787; A61N 1/0534;
(Continued)

(56) References Cited

U.S. PATENT DOCUMENTS

| 3,833,005 A | 9/1974 | Wingrove |
| 4,338,945 A | 7/1982 | Kosugi |

(Continued)

FOREIGN PATENT DOCUMENTS

| CN | 86102850 A | 11/1987 |
| EP | 1145735 | 10/2001 |

(Continued)

OTHER PUBLICATIONS

Schormans, Matthew, et al. "Practical Inductive Link Design for Biomedical Wireless Power Transfer: A Tutorial." IEEE Transactions on Biomedical Circuits and Systems, vol. 12, No. 5, 2018, pp. 1112-1130. Crossref, doi:10.1109/tbcas.2018.2846020. (Year: 2018).*

(Continued)

*Primary Examiner* — Paula J Stice
(74) *Attorney, Agent, or Firm* — McDonald Hopkins LLC

(57) ABSTRACT

A neurostimulation system is shown and described. The neurostimulation system may include a stimulation device implantable into a patient, a lead operatively coupled with the stimulation device, a first power cell providing power to the stimulation device where the first power cell is charged by an externally applied AC (High HF) magnetic field.

25 Claims, 15 Drawing Sheets

Related U.S. Application Data filed on May 22, 2013, provisional application No. 61/826,388, filed on May 22, 2013.

(51) Int. Cl.
*A61N 1/372* (2006.01)
*A61N 1/378* (2006.01)
*A61N 1/05* (2006.01)

(52) U.S. Cl.
CPC ....... *A61N 1/3787* (2013.01); *A61N 1/37235* (2013.01); *A61N 1/37518* (2017.08); *A61N 1/0534* (2013.01); *A61N 1/0539* (2013.01); *A61N 1/3752* (2013.01); *A61N 1/37247* (2013.01); *A61N 1/37252* (2013.01)

(58) Field of Classification Search
CPC ............ A61N 1/37247; A61N 1/37252; A61N 1/3752
USPC ........................................................ 607/45
See application file for complete search history.

(56) References Cited

U.S. PATENT DOCUMENTS

| | | | |
|---|---|---|---|
| 4,979,507 A | 12/1990 | Heinz | |
| 5,018,524 A | 5/1991 | Gu | |
| 5,073,544 A | 12/1991 | Seto | |
| 5,095,904 A | 3/1992 | Seligman | |
| 5,184,616 A | 7/1993 | Weiss | |
| 5,226,413 A | 7/1993 | Bennett | |
| 5,485,851 A | 1/1996 | Erickson | |
| 5,716,377 A | 2/1998 | Rise | |
| 5,724,985 A | 3/1998 | Snell | |
| 6,066,163 A | 5/2000 | Sasha | |
| 6,560,487 B1 | 5/2003 | McGraw | |
| 6,560,490 B2 | 5/2003 | Grill | |
| 6,738,668 B1 | 5/2004 | Mouchawar | |
| 6,879,860 B2 | 4/2005 | Wakefield | |
| 6,934,580 B1 | 8/2005 | Osorio | |
| 6,944,501 B1 | 9/2005 | Pless | |
| 7,003,353 B1* | 2/2006 | Parkhouse | A61N 1/3787 607/45 |
| 7,010,351 B2 | 3/2006 | Firlik | |
| 7,191,014 B2 | 3/2007 | Kobayashi | |
| 7,321,796 B2 | 1/2008 | Fink | |
| 7,483,747 B2 | 1/2009 | Gilner | |
| 7,949,397 B1 | 5/2011 | Wenzel | |
| 7,970,477 B2 | 6/2011 | Loeb | |
| 8,073,544 B2 | 12/2011 | Pless | |
| 8,355,789 B2 | 1/2013 | Werder | |
| 8,447,405 B2 | 5/2013 | Grill | |
| 8,694,106 B2* | 4/2014 | Pless | A61N 1/36178 600/544 |
| 8,792,987 B2* | 7/2014 | Stevenson | A61N 1/36135 607/45 |
| 8,798,755 B2 | 8/2014 | Grill | |
| 8,923,981 B2 | 12/2014 | Grill | |
| 9,089,708 B2 | 7/2015 | Grill | |
| 9,242,095 B2 | 1/2016 | Grill | |
| 9,259,579 B2 | 2/2016 | Grill | |
| 9,572,988 B2 | 2/2017 | Grill | |
| 9,744,363 B2 | 8/2017 | Grill | |
| 10,086,204 B2 | 10/2018 | Grill | |
| 10,086,205 B2 | 10/2018 | Grill | |
| 10,204,706 B2 | 2/2019 | Davis | |
| 2002/0077670 A1 | 6/2002 | Archer | |
| 2002/0177882 A1 | 11/2002 | Dilorenzo | |
| 2002/0177884 A1 | 11/2002 | Ahn | |
| 2003/0135248 A1 | 7/2003 | Stypulkowski | |
| 2004/0158298 A1 | 8/2004 | Gliner | |
| 2004/0243192 A1 | 12/2004 | Hepp | |
| 2004/0249422 A1* | 12/2004 | Gliner | A61N 1/36167 607/58 |
| 2005/0060009 A1 | 3/2005 | Goetz | |
| 2005/0143786 A1 | 6/2005 | Boveja | |
| 2005/0222641 A1 | 10/2005 | Pless | |
| 2005/0228453 A1 | 10/2005 | Havel | |
| 2005/0228461 A1 | 10/2005 | Osorio | |
| 2006/0015153 A1 | 1/2006 | Gliner | |
| 2006/0017749 A1 | 1/2006 | McIntyre | |
| 2006/0111759 A1* | 5/2006 | Hoyme | A61N 1/37211 607/60 |
| 2006/0212089 A1 | 9/2006 | Tass | |
| 2007/0060967 A1* | 3/2007 | Strother | A61N 1/36107 607/31 |
| 2007/0060979 A1* | 3/2007 | Strother | A61N 1/37512 128/903 |
| 2007/0067004 A1 | 3/2007 | Boveja | |
| 2007/0198066 A1 | 8/2007 | Greenberg | |
| 2007/0288064 A1 | 12/2007 | Butson | |
| 2008/0045775 A1 | 2/2008 | Lozano | |
| 2009/0036949 A1* | 2/2009 | Kokones | A61N 1/0529 607/45 |
| 2009/0082640 A1 | 3/2009 | Kovach | |
| 2009/0110958 A1* | 4/2009 | Hyde | A61N 5/0601 428/704 |
| 2009/0131993 A1 | 5/2009 | Rousso | |
| 2009/0143696 A1 | 6/2009 | Najafi | |
| 2009/0204170 A1 | 8/2009 | Hastings | |
| 2009/0221896 A1 | 9/2009 | Rickert | |
| 2009/0264954 A1 | 10/2009 | Rise | |
| 2010/0042194 A1 | 2/2010 | Ayal | |
| 2010/0121407 A1 | 5/2010 | Pfaff | |
| 2010/0121416 A1 | 5/2010 | Lee | |
| 2010/0137938 A1* | 6/2010 | Kishawi | A61N 1/36071 607/46 |
| 2010/0152807 A1* | 6/2010 | Grill | A61N 1/36082 607/45 |
| 2010/0168820 A1* | 7/2010 | Maniak | A61N 1/37247 607/63 |
| 2010/0312303 A1 | 12/2010 | York | |
| 2010/0331916 A1 | 12/2010 | Parramon | |
| 2011/0093041 A1 | 4/2011 | Straka | |
| 2011/0106213 A1* | 5/2011 | Davis | G16H 40/63 607/59 |
| 2011/0184486 A1 | 7/2011 | De Ridder | |
| 2011/0196441 A1 | 8/2011 | Ryu | |
| 2011/0270348 A1 | 11/2011 | Goetz | |
| 2012/0004707 A1 | 1/2012 | Lee | |
| 2012/0016435 A1 | 1/2012 | Rom | |
| 2012/0095524 A1 | 4/2012 | Nelson | |
| 2012/0239115 A1 | 9/2012 | Lee | |
| 2012/0245649 A1 | 9/2012 | Bohori | |
| 2012/0277828 A1* | 11/2012 | O'Connor | G16H 40/63 607/59 |
| 2012/0290041 A1 | 11/2012 | Kim | |
| 2013/0006330 A1 | 1/2013 | Wilder | |
| 2013/0102919 A1 | 4/2013 | Schiff | |
| 2013/0231715 A1 | 9/2013 | Grill | |
| 2013/0345773 A1 | 12/2013 | Grill | |
| 2014/0257428 A1 | 9/2014 | Zhu | |
| 2014/0353944 A1 | 12/2014 | Grill | |
| 2017/0361099 A1 | 12/2017 | De Ridder | |
| 2018/0064944 A1 | 3/2018 | Grill | |

FOREIGN PATENT DOCUMENTS

| | | |
|---|---|---|
| EP | 2766087 | 8/2014 |
| JP | 2008506464 A | 3/2008 |
| WO | WO2006019764 A2 | 2/2006 |
| WO | WO2010039274 | 4/2010 |
| WO | WO2014130071 A1 | 8/2014 |

OTHER PUBLICATIONS

SA/US, International Search Report and Written Opinion prepared for PCT/US2014/072112, dated Apr. 16, 2015.

International Preliminary Report on Patentability for PCT/US11/38416, dated May 3, 2012.

International Search Report/Written Opinion dated Dec. 7, 2011 in International Patent Application No. PCT/US 11/38416.

(56) References Cited

OTHER PUBLICATIONS

International Search Report and the Written Opinion of the International Searching Authority, PCT/US2013/046183, Duke University, dated Oct. 4, 2013.
International Search Report and the Written Opinion of the International Searching Authority, PCT/US2012/059787, Duke University, dated Jan. 4, 2013.
International Preliminary Examination Report, PCT/US2009/05459, Duke University, dated Jan. 11, 2011.
International Search Report and the Written Opinion of the International Searching Authority, PCT/US2009/05459, Duke University, dated Dec. 3, 2009.
Extended European Search Report, Application No. 09818122.5-1652/2340078, Duke University, dated Aug. 2, 2013.
Rubin, Jonathan et al., High Frequency Stimulation of the Subthalamic Nucleus Eliminates Pathological Thalamic Rhythmicity in a Computational Model, Journal of Computational Neuroscience, vol. 16, pp. 211-235, 2004.
McIntyre, Cameron et al., Cellular Effects of Deep Brain Stimulation: Model-Based Analysis of Activation and Inhibition, J. Neurophysiol, vol. 91, pp. 1457-1469, 2004.
Birdno, Merrill Jay, Analyzing the Mechanisms of Action of Thalamic Deep Brain Stimulation: Computational and Clinical Studies, Ph. D. Dissertation, Department of Biomedical Engineering, Duke University, Durham, NC, USA, Aug. 2009.
Constantoyannis, Constantine, et al., Tremor Induced by Thalamic Deep Brain Stimulation in Patients with Complex Regional Facial Pain, Movement Disorders, vol. 19, No. 8, pp. 933-936, 2004.
Benabid, Alim et al., Long-term suppression of tremor by chronic stimulation of the ventral intermediate thalamic nucleus. The Lancet, vol. 337, pp. 403-406, Feb. 16, 1991.
Davis, Lawrence, Handbook of Genetic Algorithms, Van Nostrand Reinhold, NY, pp. 1-402, 1991.
Dorval, Alan et al., Deep Brain Stimulation Alleviates Parkinsonian Bradykinesia by Regularizing Pallidal Activity, J. Neurophysiol, vol. 104, pp. 911-921, 2010.
Fogelson, Noa et al., Frequency dependent effects of subthalamic nucleus stimulation in Parkinson's disease, Neuroscience Letters 382, 5-9, 2005.
Grefenstette, John, Optimization of Control Parameters for Genetic Algorithms, IEEE Transactions on Systems, Man, and Cybernetics, vol. SMC-16, No. 1, pp. 122-128, Jan./Feb. 1986.
Feng, Xiao-jiang et al., Optimal Deep Brain Stimulation of the Subthalamic Nucleus—a Computational Study, Journal of Computational Neuroscience, 23(3):265-282, Jan. 9, 2007.
Grill, W.M. et al., Effect of waveform on tremor suppression and paresthesias evoked by thalamic deep brain stimulation (dbs). Society for Neuroscience Abstract 29, 2003.
Kuncel, Alexis et al., Clinical Response to Varying the Stimulus Parameters in Deep Brain Stimulation for Essential Tremor, Movement Disorders, vol. 21, No. 11, pp. 1920-1928, 2006.
Kupsch, A. et al., The effects of frequency in pallidal deep brain stimulation for primary dystonia, J. Neurol 250:1201-1205, 2003.
Finnerman, Lars et al., The cerebral oscillatory network of parkinsonian resting tremor, Brain, 126, pp. 199-212, 2003.
Limousin, Patricia et al., Effect on parkinsonian signs and symptoms of bilateral subthalamic nucleus stimulation, The Lancet, vol. 345, pp. 91-95, Jan. 14, 1995.
Brocker, David, et al., Improved Efficacy of Temporally Non-Regular Deep Brain Stimulation in Parkinson's Disease, Department of Biomedical Engineering, Duke University, Durham NC 27708-0281, pp. 1-34. 2012.
Extended European Search Report for Application 13875748.9 PCT/US2013046183, dated Mar. 9, 2016, European Patent Office, Germany.
International Searching Authority, US Patent Office; International Search Report and Written Opinion for PCT/US2014/038809, dated Dec. 15, 2014, 19 pages.
Feng et al. "Toward closed-loop optimization of deep brain stimulation for Parkinson's disease: concepts and lessons from a computational model." J. Neural Eng. 4 (2007) L14-L21. Feb. 23, 2007.
So et al. "Relative contributions of local cell and passing fiber activation and silencing to changes in thalamic fidelity luring deep brain stimulation and lesioning: a computational modeling study". Comput Neurosci (2012) 32:499-519. Oct. 5, 2011.
Kent et al. "Instrumentation to Record Evoked Potentials for Closed-Loop Control of Deep Brain Stimulation". Conf Proc IEEE Eng Med Biol Soc. 2011; 2011: 6777-6780. doi:10.1109/IEMBS.2011.6091671.
Dorval et al. "Deep Brain Stimulation that Abolishes Parkinsonian Activity in Basal Ganglia Improves Thalamic Relay Fidelity in a Computational Circuit". Conf Proc IEEE Eng Med Biol Soc. 2009; 1: 4230. doi:10.11091EMB5.2009.5333611.
European Patent Office, Supplementary European Search Report, EP14874436, dated Jan. 17, 2018.
European Patent Office, European Search Report, EP 17001653, dated Jan. 4, 2018.

* cited by examiner

DEEP BRAIN STIMULATOR AND METHOD OF USE

CROSS-REFERENCE TO RELATED APPLICATIONS

This application claims priority to U.S. Provisional Application No. 61/826,361 entitled "IMPLANTABLE DEEP BRAIN STIMULATION LEAD," filed on May 22, 2013; U.S. Provisional Application No. 61/826,388 entitled "IMPLANTABLE NEUROSTIMULATOR," filed on May 22, 2013; and U.S. Provisional Application No. 61/826,384, entitled "DEEP BRAIN STIMULATION SYSTEM," filed on May 22, 2013, each of which is hereby incorporated by reference in its entirety.

FIELD OF USE

The present invention relates to systems and methods for providing deep brain stimulation, and more particularly to systems and methods of deep brain stimulation to treat a neurological condition or symptom.

BACKGROUND

Neurostimulation, i.e., neuromuscular stimulation (the electrical excitation of nerves and/or muscle that may directly elicit the contraction of muscles) and neuromodulation stimulation (the electrical excitation of nerves, often afferent nerves, to indirectly affect the stability or performance of a physiological system) and brain stimulation (the stimulation of cerebral or other central nervous system tissue) can provide functional and/or therapeutic outcomes. While existing systems and methods can provide remarkable benefits to individuals requiring neurostimulation, many quality of life issues still remain. For example, existing systems are, by today's standards, relatively large and awkward to manipulate and transport. There exist both external and implantable devices for providing neurostimulation in diverse therapeutic and functional restoration indications. The operation of these devices typically includes the use of an electrode placed either on the external surface of the skin and/or a surgically implanted electrode.

Deep Brain Stimulation (DBS) has been found to be successful in treating a variety of brain-controlled disorders, including movement disorders. Generally, such treatment involves placement of a DBS type lead into a targeted region of the brain through a burr hole drilled in the patient's skull, and the application of appropriate stimulation through the lead to the targeted region.

Although effective, conventional high frequency stimulation generates stronger side-effects than low frequency stimulation, and the therapeutic window between the voltage that generates the desired clinical effect(s) and the voltage that generates undesired side effects decreases with increasing frequency. Precise lead placement therefore becomes important. Further, high stimulation frequencies increase power consumption. The need for higher frequencies and increased power consumption shortens the useful lifetime and/or increases the physical size of battery-powered implantable pulse generators. The need for higher frequencies and increased power consumption requires a larger battery size, and frequent charging of the battery, if the battery is rechargeable.

The art of electrical stimulation would benefit from improved systems and methods of applying electrical neurostimulation.

SUMMARY

A system to provide neurostimulation to a patient is shown and described. An implantable electrical stimulator is a central element of a system used to provide neurostimulation to a patient with an implanted or percutaneous electrode. The other accessories of the implantable stimulator are a patch assembly, one or more cables, which may be provided in shorter or longer versions, and one or more implantable or percutaneous leads (each including one or more electrodes) and its interface connector.

In one aspect of the invention, the system comprises an implantable electrical stimulator. The electrical stimulator may be coupled to a mounting patch assembly in any appropriate manner. A cable may couple the electrical stimulator to one or more implantable or percutaneous leads (each including one or more electrodes). The electrical stimulator may also be coupled to a connector in any appropriate manner, including, for example, by a second cable.

The Implantable Deep Brain Stimulation Lead may deliver stimulation through multiple electrical contacts to brain tissue. The lead may have four or eight independent electrical channels. Each channel consists of a proximally-located electrical contact and a distally-located electrode. The electrodes may be cylindrical in shape. In some embodiments, a single cylindrical space may have two contacts, each occupying one half of the cylindrical surface. The multitude of electrodes may permit current steering which may be controlled by a neurostimulator.

A lead connector configuration may be designed to interface with a header of a primary cell or secondary cell neurostimulator. The connector may be cylindrical and straight or it may be slightly curved so that it can interface with a header that is curved due to tangential alignment with a cylindrical neurostimulator. If space requirements prevent an in-line cylindrical connector, a rectangular pin and socket style electrical connector may be used. Further, the lead extension or connector within the header of the neurostimulator may be compatible with multiple vendors' connector size, contact quantity and spacing to allow for interchangeable use.

In an embodiment, a neurostimulation system may include a stimulation device and at least one lead connected to the stimulation device. The system includes a first power cell configured to power the stimulation device. The power cell may be rechargeable by the transcutaneous application of an AC magnetic field. The system may optionally include a second power cell. The stimulation device may be configured to deliver a series of pulses. The stimulation device may be capable of reducing the frequency or pulse length of the pulses.

A medical stimulation system having a stimulator implantable in a patient's nervous system. The stimulator may be configured to transmit an electrical signal including a repeating succession of pulse trains. Each pulse train may include a plurality of single pulses and embedded multiple pulse groups, with non-random differing inter-pulse intervals between the single pulses and the embedded multiple pulse groups. The stimulator may be connected to a clinical programmer through a wireless communications subsystem. The clinical programmer may be operatively and wirelessly coupled with the stimulator. The clinical programmer may control the electrical signal of the stimulator by modifying the repeating succession of pulse trains. Modifying the repeating succession of pulse trains may improve efficacy of the electrical signal. The stimulator may include a battery with a life span. Modifying the repeating succession of pulse trains may increase the life span of the battery. The clinical programmer may be operated through an electronic computing device. Also, the clinical programmer may have sensors to collect data. The neurostimulation system may also include a remote operatively and wirelessly coupled with the stimulator.

A neurostimulation system is shown and described. The neurostimulation system may include a stimulation device implantable into a patient, a lead operatively coupled with the stimulation device, a first power cell providing power to the stimulation device where the first power cell is charged by an externally applied AC (High HF) magnetic field.

A neurostimulation system may include a stimulator implantable in communication with a patient's nervous system, the stimulator configured to generate an electrical signal, and a clinical programmer operatively and wirelessly coupled with the stimulator, the clinical programmer controls the electrical signal of the stimulator by modifying at least one characteristic of the electrical signal.

A neurostimulation system may include an electrical stimulator, at least one lead, the leading having at least one electrode, where the lead is implantable within a patient, and a charger in communication with the electrical stimulator using an UHF telemetry wireless link.

A neurostimulation system may include an implantable electrical stimulator, the electrical stimulator configured to apply a first electrical signal, and a remote operatively coupled with the electrical stimulator, the remote configured to change the first electrical signal to a second electrical signal, where the second electrical signal has a cost-benefit relationship with the first electrical signal.

A neurostimulation system for treating a neurological condition may include an implantable electrical stimulator configured to apply a first stimulus pattern, a power source coupled with the implantable electrical stimulator to providing power to the implantable electrical stimulator, and a programmer operatively coupled with the electrical stimulator, the programmer configured to modify the implantable electrical stimulator to apply a second stimulus pattern, where the second stimulus pattern has increased effectiveness at reducing the neurological condition while reducing an operating life of the power source.

An implantable neurostimulator may include a secondary cell configured to receive externally generated power to recharge the secondary cell, and a case housing the secondary cell, the housing configured to be placed in a recess in a cranium of a patient.

BRIEF DESCRIPTION OF THE DRAWINGS

Operation of the invention may be better understood by reference to the following detailed description taken in connection with the following illustrations, wherein.

DETAILED DESCRIPTION

Reference will now be made in detail to exemplary embodiments of the present teachings, examples of which are illustrated in the accompanying drawings. It is to be understood that other embodiments may be utilized and structural and functional changes may be made without departing from the respective scope of the teachings. Moreover, features of the various embodiments may be combined or altered without departing from the scope of the teachings. As such, the following description is presented by way of illustration only and should not limit in any way the various alternatives and modifications that may be made to the illustrated embodiments and still be within the spirit and scope of the teachings.

A. Implantable Deep Brain Stimulation System

Figure 1:
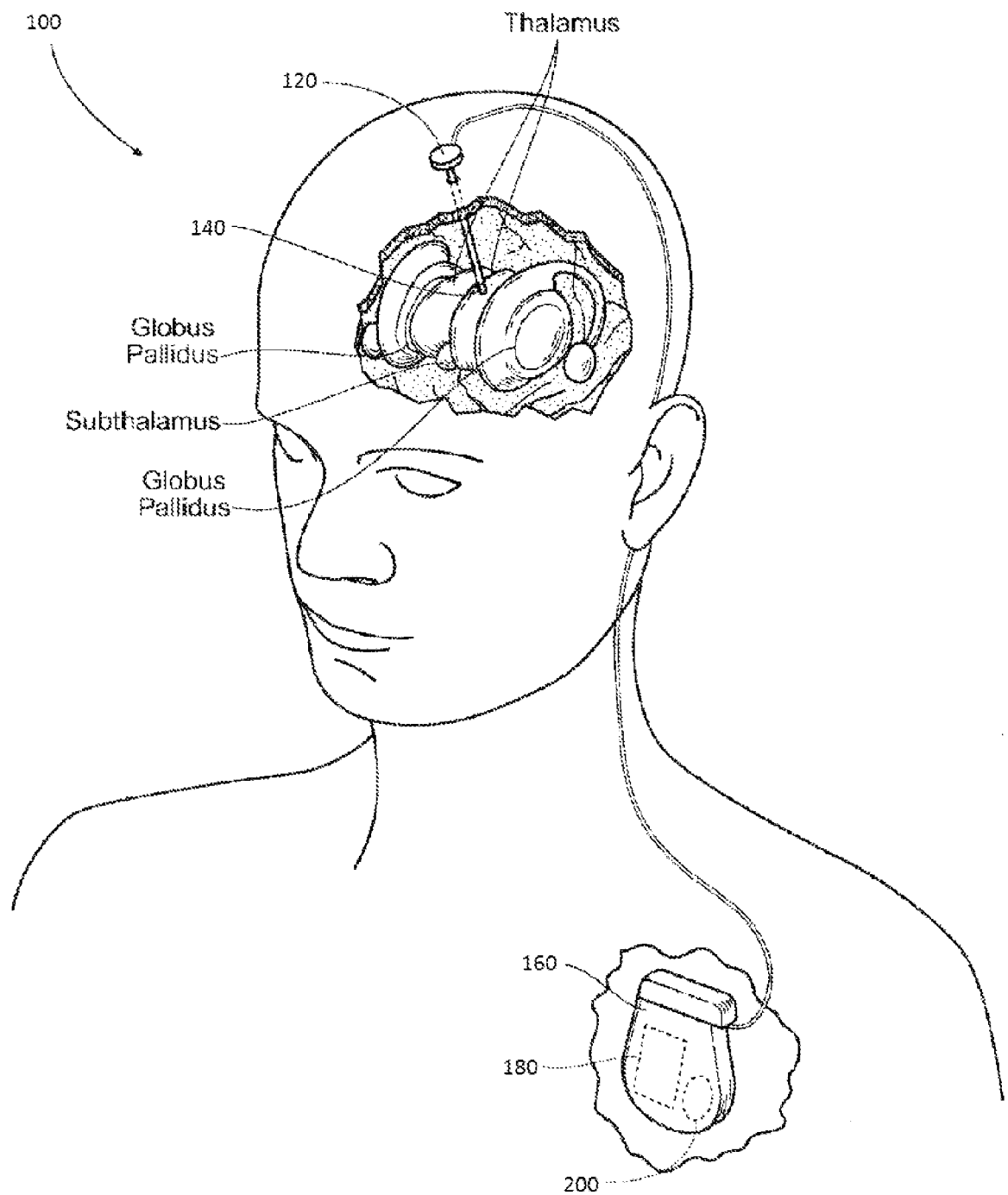
FIG. 1 is an anatomic view of a system for stimulating tissue of a central nervous system that includes an lead implanted in brain tissue coupled to a pulse generator programmed to provide non-regular (i.e., not constant) pulse patterns or trains, in which the interval between electrical pulses (the inter-pulse intervals) changes or varies over time.

Turning now to the figures, FIG. 1 depicts is a system 100 for stimulating tissue of the central nervous system. The system includes a lead 120 placed in an appropriate position in contact with or in operative communication with central nervous system tissue. In the illustrated embodiment, the lead 120 may be implanted in a region of the brain, such as the thalamus, subthalamus, or globus pallidus for the purpose of deep brain stimulation. However, it should be understood, the lead 120 may be implanted in, on, or near the spinal cord; or in, on, or near a peripheral nerve (sensory or motor) for the purpose of selective stimulation to achieve a therapeutic purpose.

The distal end of the lead 120 may carry one or more electrodes 140 to apply electrical pulses to the targeted tissue region. The electrical pulses are supplied by a pulse generator 160 operatively coupled to the lead 120.

In the illustrated embodiment, the pulse generator 160 may be implanted in a suitable location remote from the lead 120, e.g., in the shoulder region. It should be appreciated, however, that the pulse generator 160 may be placed in other regions of the body or externally.

When implanted, the case of the pulse generator may serve as a reference or return electrode. Alternatively, the lead 120 may include a reference or return electrode (comprising a bi-polar arrangement), or a separate reference or return electrode can be implanted or attached elsewhere on the body (comprising a mono-polar arrangement).

The pulse generator 160 may include an on-board, programmable microprocessor 180 that may carry embedded code. The code may express pre-programmed rules or algorithms under which a desired electrical stimulation waveform pattern or train may be generated and distributed to the electrode(s) 140 on the lead 120. According to these programmed rules, the pulse generator 160 may direct the prescribed stimulation waveform patterns or trains through the lead 120 to the electrode(s) 140, which may serve to selectively stimulate the targeted tissue region. The code may be preprogrammed by a clinician to achieve the particular physiologic response desired and may be re-programmable as described in more detail below. an on-board battery 200 may supply power to the microprocessor 180.

B. Rechargeable Neurostimulator System

Figure 2:
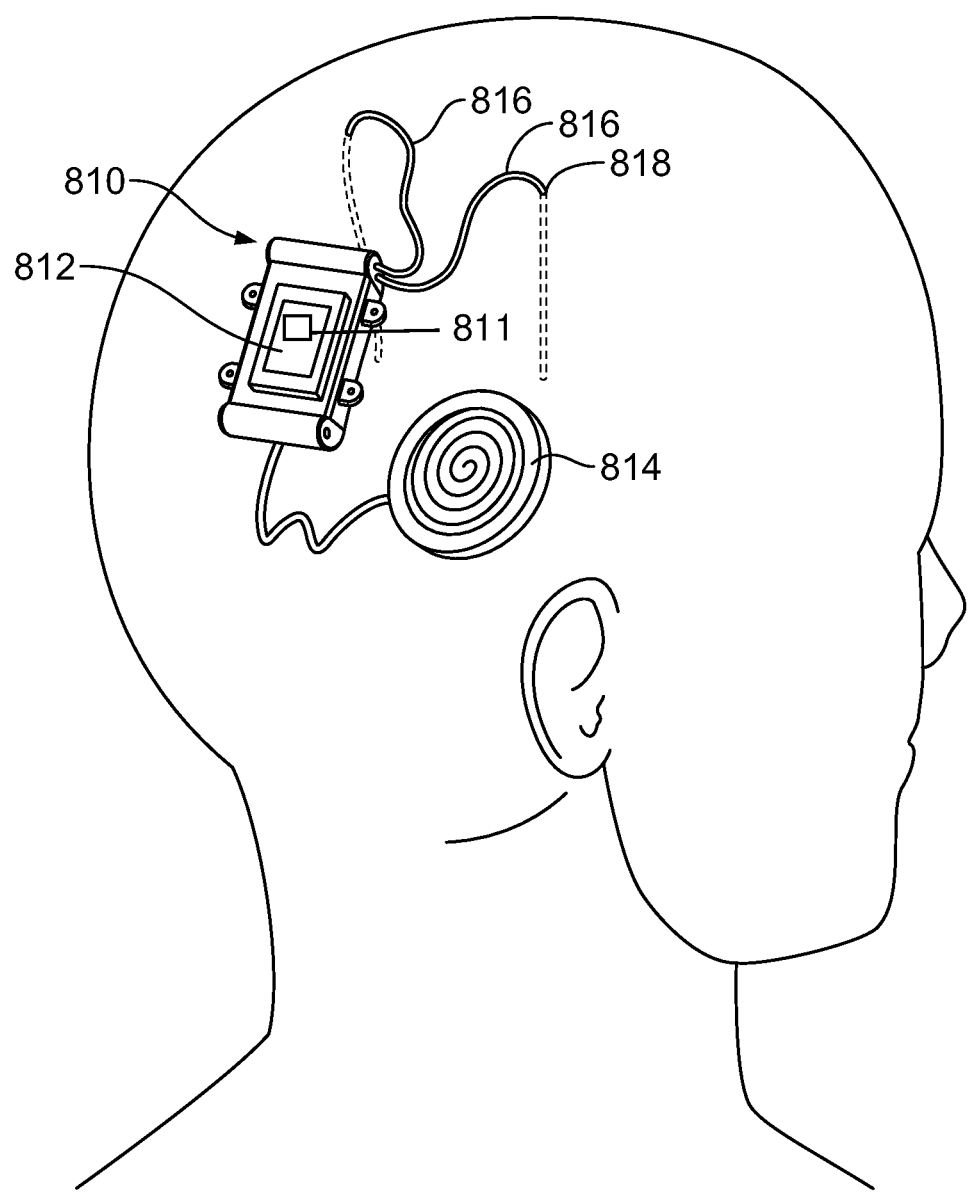
FIG. 2 is a deep brain implantable rechargeable neurostimulator.

A neurostimulator 810 is depicted in FIG. 2. The neurostimulator 810 may be a rechargeable neurostimulator 810 of any appropriate configuration. The neurostimulator 810 may be configured to generate novel patterns of stimulation, as further described below. The stimulation may be applied using conventional deep brain implants or new innovative deep brain implants.

The patterns of stimulation may be a sequence or a schedule of pulse-to-pulse intervals that may provide an efficient activation of the surrounding neural structures. These pulse by pulse variations in instantaneous frequency may provide an effective activation of the neural structure treatment at a lower average frequency than a regular (fixed frequency) stimulus pulse train of the same effectiveness at activating the neural structure. This lower average stimulus frequency may directly correspond to reduced power consumption and a correspondingly longer operating life for the implantable neurostimulator generating the stimulus.

Additionally, the same ratios of pulse-to-pulse interval may be maintained while scaling to a higher average frequency (i.e., a shorter average pulse-to-pulse interval). This temporal pattern of stimulus pulses may provide a more effective stimulation (greater treatment efficacy for underlying disease mechanisms such as Parkinson Disease) than regular stimulus waveform with comparable undesirable side effects.

The timing of the stimulus pulses in a modern implantable neurostimulator 810 (such as DBS implants) may be determined by micro programmed semiconductor devices. These devices are essentially microcontroller cores that control the neurostimulation hardware through use of digital and/or analog input-output ports, programmable timers/counters, and serial/telemetry interfaces.

The use of a micro programmable device (or core inside a custom Application Specific Integrated Circuit (ASIC)) as the primary controller inside a neurostimulator may allow an existing device to implement the novel patterns of stimulation with only changes to the program of the embedded microcontroller; i.e., with a change to the embedded software also called firmware. In some implantable neurostimulators this change of software (or extensible stimulus parameter definitions) may be possible through the wireless telemetry (UHF or inductive coupling) of the implant.

The neurostimulator 810 may incorporate a primary cell or a secondary cell 812. The implantable neurostimulator 810 with a secondary cell 812 may include components for receiving externally generated power in order to recharge the power cell. In an embodiment, the secondary cell may be a Lithium Ion cell; however, the present teachings are not limited to such. Any appropriate cell or battery may be used without departing from the present teachings.

The neurostimulator 810 may be used to treat diseases and conditions responsive to deep brain stimulation or cortical brain stimulation. The present teachings, however, are not limited to such. The present neurostimulator 810 may be used to treat any appropriate condition or provide any appropriate therapy.

The novel patterns of stimulation may provide a significant (such as greater than 2:1) reduction in the power consumption for neuro stimulation 810 of a given efficacy. This significant reduction in power requirements may allow an implantable primary cell neurostimulator 810 to be developed with a smaller size and an operating life comparable to 'conventional' neurostimulators (using regular, fixed frequency pulse trains). Similarly, the novel patterns of stimulation may also be applied to a secondary cell implantable neurostimulator 810 to reduce the size of that implant. This may make possible alternative and novel placements of the neurostimulator 810, including: in a hole or patch of skull bone (cranium) removed or carved out surgically, from the skull above or at the level of the neck. By way of a non-limiting example, the neurostimulator 810 of the present teachings may be small enough and formed in a shape that mates with the size and shape of a burr hole formed in a patient's cranium. This may allow for shorter leads as they would be required to travel less of a distance through the body than the traditional leads used with neurostimulators implanted in a chest of patient. Further still, less of the body of the patient would undergo surgery as only the head area would require surgery as opposed to the chest and neck of traditional neurostimulators.

Further, in addition to simplifying the attachment of charging coils, these locations also provide advantages of less surgical tunneling of the DBS leads and avoiding or reducing the severity of motion and reliability concerns associated with neck motions. Further still, this configuration may allow for alternative shapes of the neurostimulator 810. By way of a non-limiting example, a surgeon may produce a generally circular bore in the skull bone (cranium) of a patient having a predetermined diameter. The neurostimulator 810 may be generally circular and may have a diameter such that the neurostimulator 810 generally fills the circular bore of the patient. That is the diameter of the circular bore may generally match the diameter of the neurostimulator 810.

As shown in FIG. 2, the neurostimulator 810 may support two channels (two separate leads); i.e., electrodes located on two separate electrode catheters 816, 818 going in two different locations in or on the brain. It is, of course, possible to use the neurostimulator 810 with only one of the two leads 816, 818 while the other is plugged or otherwise protected from body fluids and tissues. Further, the neurostimulator 810 is not limited to only having two leads any appropriate number of leads may be utilized.

The neurostimulator 810 may include a capsule or case 820, such as a metal case. The case 820 may provide a hermetic seal of the neurostimulator electronics including a battery (cell). All electrical connection through the case may be made by metal-glass or metal-ceramic feedthroughs. The case may be formed of a material that will not deteriorate within the body or leach elements in the body, i.e., it may be biocompatible.

The power recovery coil 814 (the multi-turn coil that recovers electrical power from an externally generated HFAC magnetic field) of a rechargeable neurostimulator 810 may be located inside the hermetically sealed capsule 820 or outside. If located outside, it may be implemented as a thin coil enclosed in a soft material such as silicone rubber. It may be insert molded into the silicone rubber and assembled between sheets of separated cured or formed silicone rubber.

The capacity of the secondary cell 814 may be selected such that the neurostimulator 810 can operate for at least one week before needing recharging for most patients. Similarly, there may be likely little need to have a cell capacity that provides much more than one month of operation for most patients. However, the present teachings are not limited to a specific cell capacity—any appropriate cell capacity may be utilized.

The metal of the case 820 may have an alloy of titanium. The alloying (of titanium or a suitable stainless steel) may serve two purposes: it may provide a greater strength or hardness and it may increase the electrical resistance. The increased electrical resistance may allow less heating of the case in the presence of an HF magnetic field and may allow a high field within the case where the power recovery coil 814 of the rechargeable neurostimulator converts that HF magnetic field into electrical power to recharge the secondary cell. The external charging system may generate the HF magnetic field in a coil or coil placed over or near the neurostimulator 810. This may be an inductively coupled charging system.

Neurostimulator 810 may incorporate a UHF (Ultra High Frequency: 300 MHz to 3 GHz) radio telemetry system. The UHF radio may use an antenna in a plastic header of the neurostimulator 810. The wireless telemetry system may operate in the MICS (Medical Implant Communications Service) band. The wireless telemetry may be usable close to the patient (e.g., 1-5 meters). The wireless telemetry system may incorporate a unique identification number (e.g., a serial number) as part of the message packages that identifies the neurostimulator 810 for which or from which the message originated or is intended. These message packages (or the broader communication process for some or all commands) may also incorporate provisions for qualifying and authenticating the message and sender.

The wireless telemetry may be used for: programming and retrieving stimulus parameters, programming or modifying operating firmware (embedded software within the neurostimulator), retrieving the operating status and battery status of the neurostimulator, retrieving data about the strength of the HF magnetic field generated by the external charger for purposes of adjusting the location or strength of the external HF magnetic field.

The UHF receiver system and its firmware may power up its receiver circuitry only rarely to search or 'sniff' the predetermined frequency or frequencies for the presence of an RF signal. This may be necessary to minimize the energy expended in the receiving circuitry. These rare events may be conducted periodically (i.e., on a scheduled basis such as once every 1-30 seconds) or it may be conducted after the presence of a large static or HF magnetic field is detected. Such a "wake up" event may be caused by the user passing a magnet or their external device (a Patient Controller, a Programmer's exciter, or the Charging cap) over the implant. The DC magnetic field sensor (perhaps a magnetic reed switch or a Hall effect sensor) may also be used to suspend the operation of the neurostimulator 810; and the HF magnetic field sensor may be the power recovery coil (a coil of wire wound near the perimeter of the neurostimulator 810) that is used to recover the electrical power for recharging the cell/battery.

The wireless communications protocol may allow the operation of the patient controller and the external charger at the same time. Similarly, multiple patients may be using their wireless systems at the same time with no risk of crossed or corrupted messages being used.

The neurostimulator 810 may have circuitry incorporating a programmable microprocessor/microcontroller (both referred to here as an MCU). This MCU or these MCUs may deliver differing stimulation based on the stimulus parameters, patterns, and regimes programmed by the clinician. Furthermore, the patient may through the use of their patient controller make changes to the stimulation they are receiving within a range of choices programmed by the clinician. The MCU might be a separate semiconductor device or it might be implemented as a collection of circuitry in an ASIC (Application Specific Integrated Circuit) or a more broadly programmable semiconductor device.

In addition to the usual, fixed frequency stimulation, the neurostimulator 810 may also support novel, non-regular patterns of stimulation. Additionally, the neurostimulator 810 may support pulse by pulse variations in pulse duration or amplitude in addition to pulse-to-pulse timing variations. In one embodiment, the neurostimulator 810 stores a plurality of electrical signals. In another embodiment, the plurality of electrical signals includes a plurality of non-regular pulse timing in semiconductor memory 811.

The stimulus patterns and parameters programmed by the clinician and selectable by the patient may be intended to offer patients the option of temporarily selecting a stimulation that has increased effectiveness at reducing the primary symptoms of their disease or condition even if that choice results in reduced operating life or increases in side effects of the stimulation. This on the spot patient choice of this treatment/side effects tradeoff may allow the patient to optimize his/her treatment for his/her personal needs and circumstances.

In addition to modifying the per pulse charge, the patient selectable changes to the stimulation may include the average frequency of the novel, non-regular patterns of stimulation, such as those disclosed in U.S. Pat. No. 8,447,405, which is incorporated herein by reference. The present teachings, however, are not limited to just the non-regular pattern of stimulation. The present teachings may be applied to any stimulation pattern, including, without limitation, non-regular, non-random, differing pulse patterns, regular pulse patterns, a combination of the foregoing and the like.

The secondary cell neurostimulator may be sized, shaped, and configured for placement in and securing to the cranium (skull), as shown in FIGS. 2-5. In such applications, the cranium may be cutout or carved to make a pocket for the neurostimulator 810.

Figure 3:
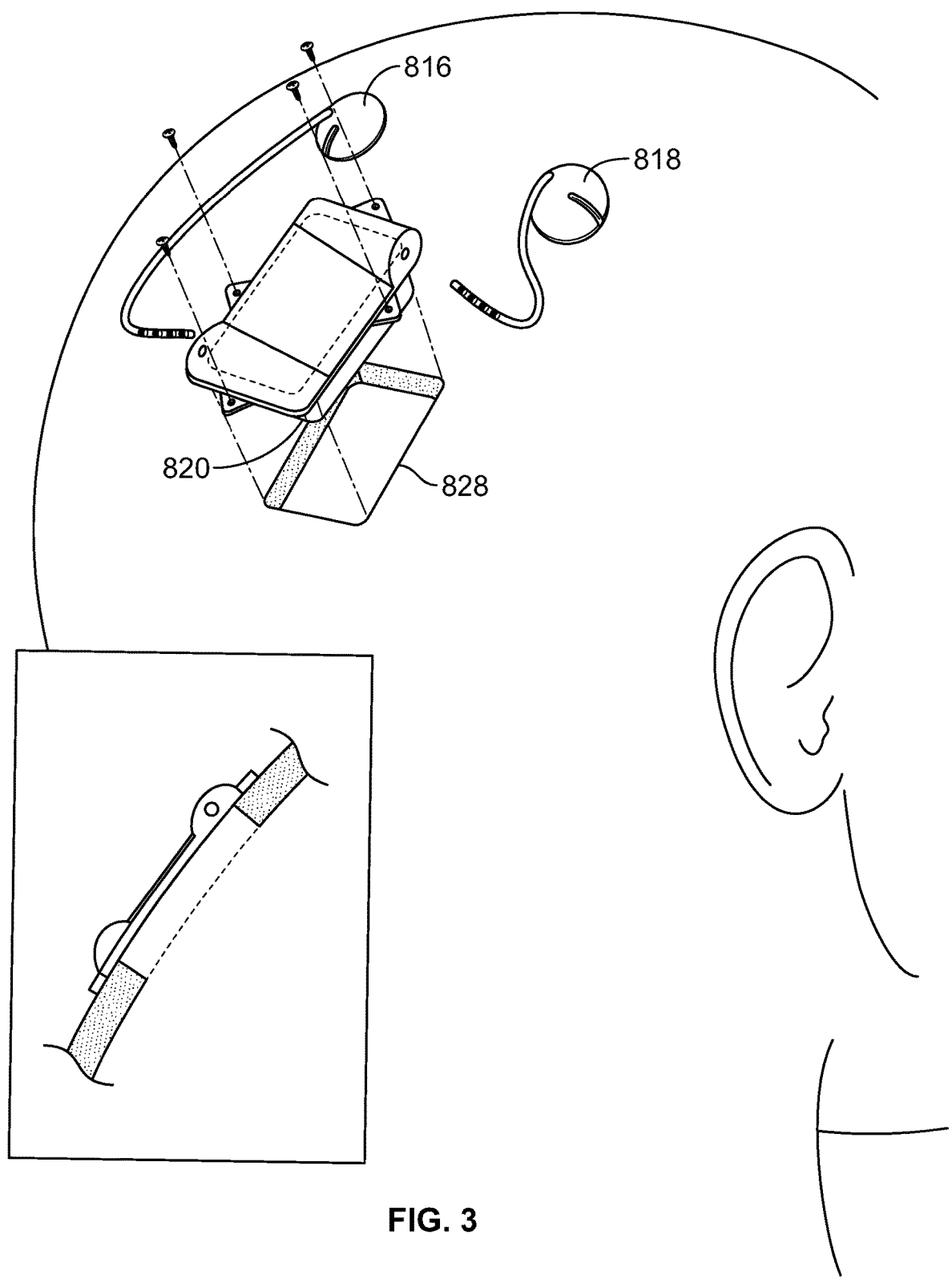
FIG. 3 is an alternative view of a deep brain implantable rechargeable neurostimulator.
Figure 4:
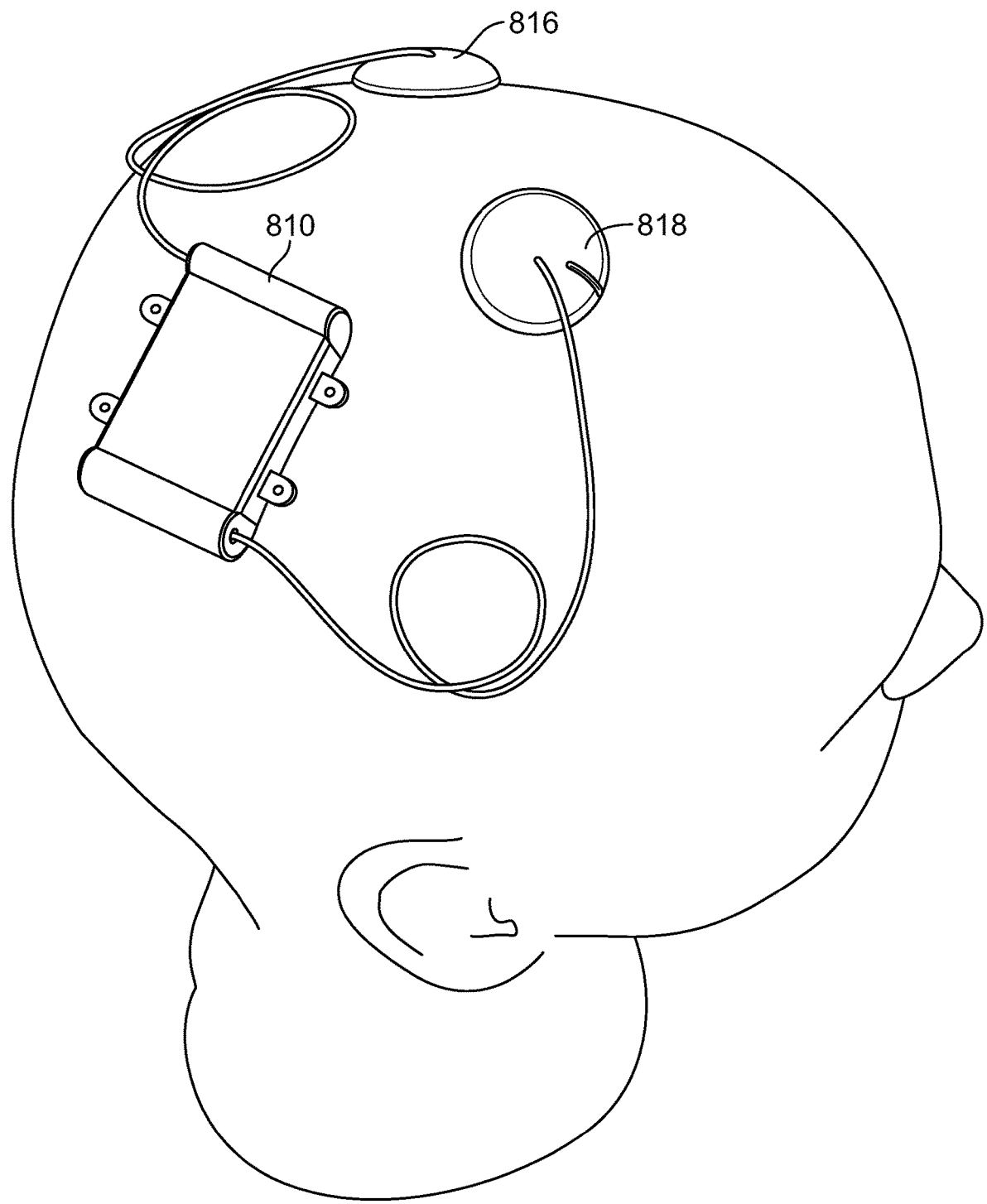
FIG. 4 is a side view of a deep brain implantable rechargeable neurostimulator.
Figure 5:
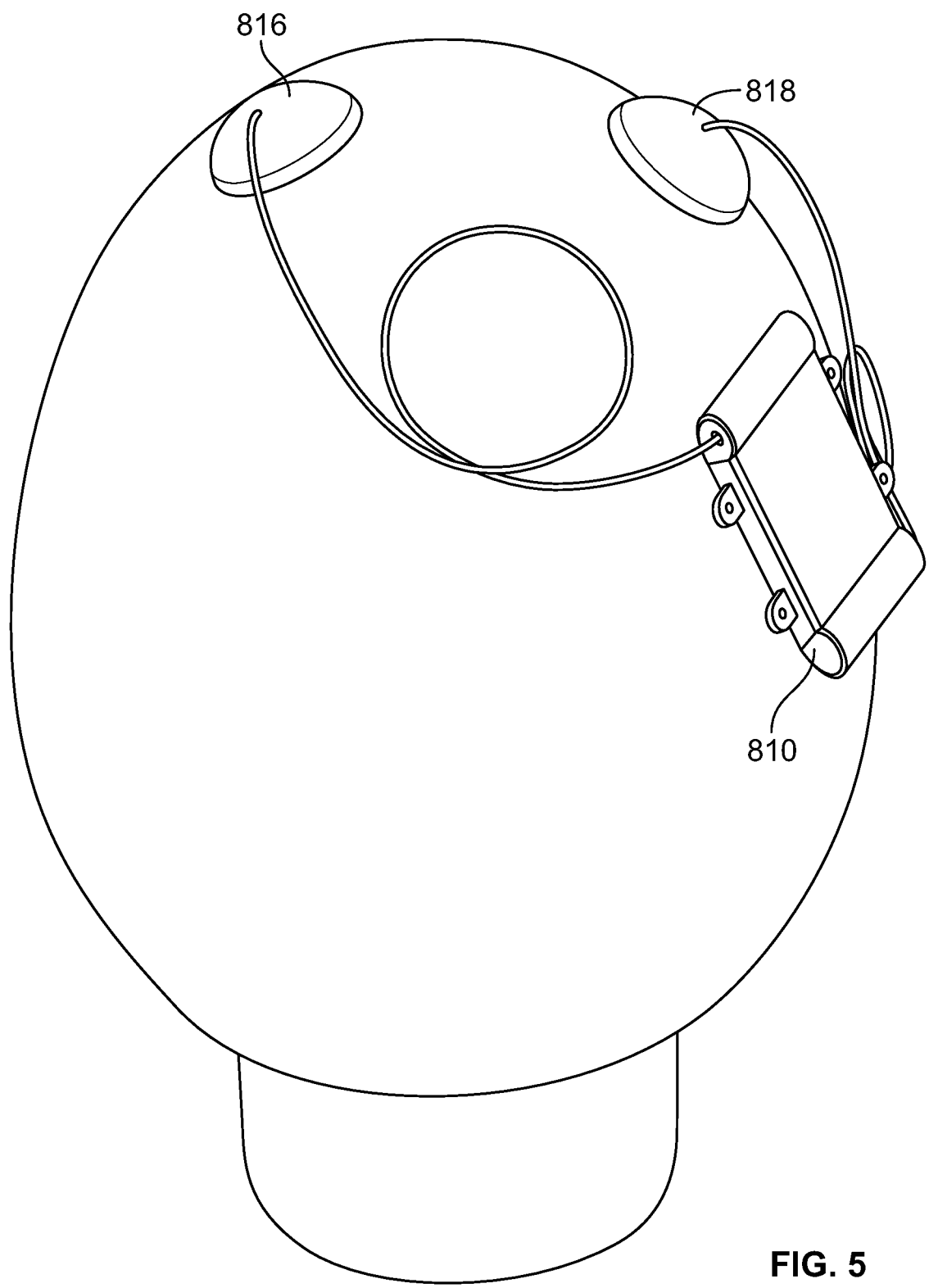
FIG. 5 is a rear view of a deep brain implantable rechargeable neurostimulator.

A cranially mounted neurostimulator 810 may have a curved case 820 to better match the contour of the cranium where it will be placed. Such a case may also include tabs, flanges, eyelets, or wings that secure the neurostimulator 810 to the skull and provide mechanical protection to the brain tissue underneath the neurostimulator 810; i.e., to prevent externally applied forces from pushing the neurostimulator 810 toward the underlying brain tissue. These mounting tabs/flanges/wings/eyelets may include holes for screws to secure to the cranium. Such a case may be largely square or rectangular in shape. Exemplary configurations of these mounting options are shown in FIGS. 3-5. It should be understood, however, that these are merely exemplary configurations and are not intended to be exclusive.

Figure 6:
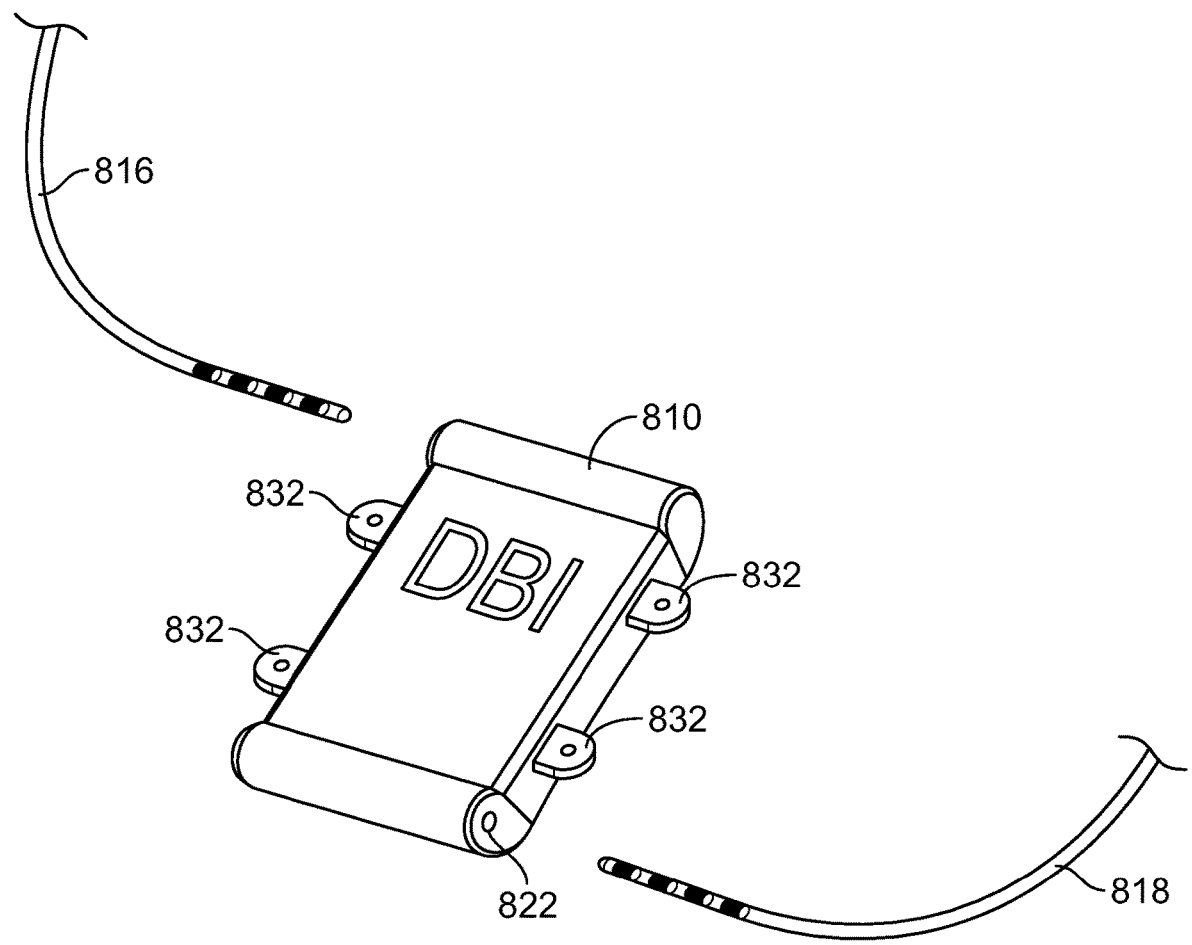
FIG. 6 is a neurostimulator with two leads.

As shown in FIG. 6, connection to the leads may be made via connectors 822 (receptacles) located in polymer headers at ends or sides of the case and connected to the electronics via feedthroughs. These connectors may be of any appropriate configuration. These lead receptacles may be at the top edges of the neurostimulator 810 (i.e., at or above the skull line) to simplify the connection to and routing of the leads.

It is also possible that the neurostimulator 810 may have pigtail leads exiting the headers. Further, the removable connection to the electrode/lead may be made not in the header but in an inline connector.

The neurostimulator 810 may be wholly or partially located in a cranial burr hole 828. Such a neurostimulator 810 may include a cylindrical body 830 protruding into the burr hole 828 and may include a tab or flange 832 that extends over the surrounding intact or shaved down cranium to secure the neurostimulator 810 and protect the underlying brain tissue; i.e., to prevent externally applied forces from pushing the neurostimulator 810 toward the underlying brain tissue. This flange 832 may include holes 834 for screws to secure to the cranium. In an embodiment, the neurostimulator 810 or case 830 may fit into the burr hole 828 with approximately 60% of the case 830 positioned below the cranial surface and approximately 40% of the case 830 positioned above the surface. These are merely exemplary, however, and the present teachings are not limited to these percentages. Any appropriate amount of the neurostimulator 810 or case 830 may fit into the burr hole 828 and be positioned above or below the cranial surface.

Figure 7:
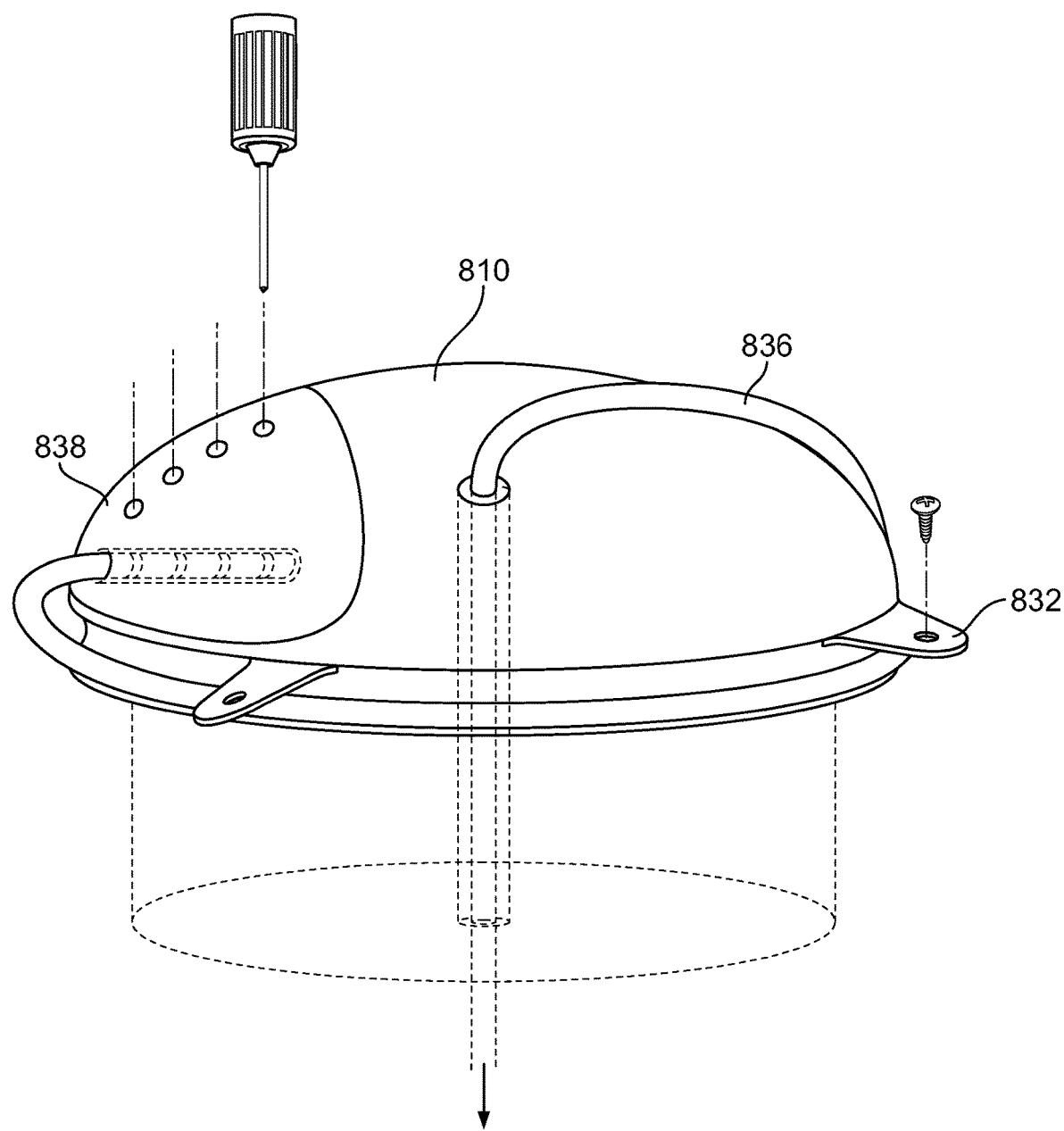
FIG. 7 is a neurostimulator located in a lead burr hole.
Figure 8:
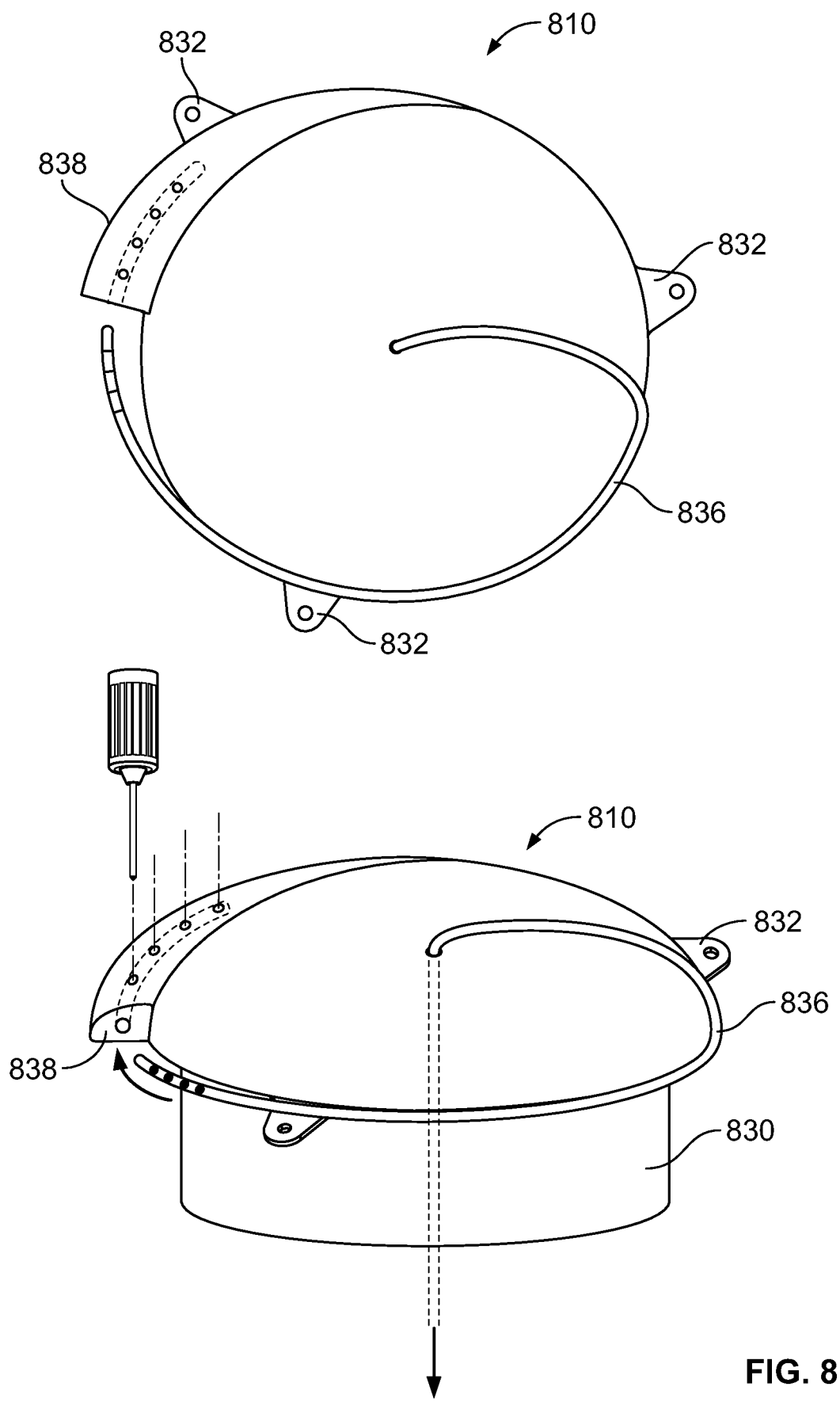
FIG. 8 is a neurostimulator with a tangential header.

The neurostimulator 810 may be located in the lead burr hole in the case of deep brain stimulation. In this case the neurostimulator 810 may support one channel (one lead). In this case the neurostimulator 810 may provide both bend relief for the DBS lead 836 as well as housing the neurostimulator 810. The DBS lead 836 may connect to the neurostimulator 810 by way of a header 838 that may be screwed or otherwise connected to the neurostimulator 810. Two possible implements are shown in FIGS. 7 and 8. In one the DBS lead 836 may pass generally through the center of the neurostimulator 810 and in the other it may be held in a thin nest that may be placed into the burr hole before the neurostimulator 810 and routes the lead to the side of the neurostimulator 810.

In a cylindrical neurostimulator 810, the lead header may be located along the outer circumference of the flange or top and provide an integral strain/bend relief as shown in FIG. 7.

Figure 9:
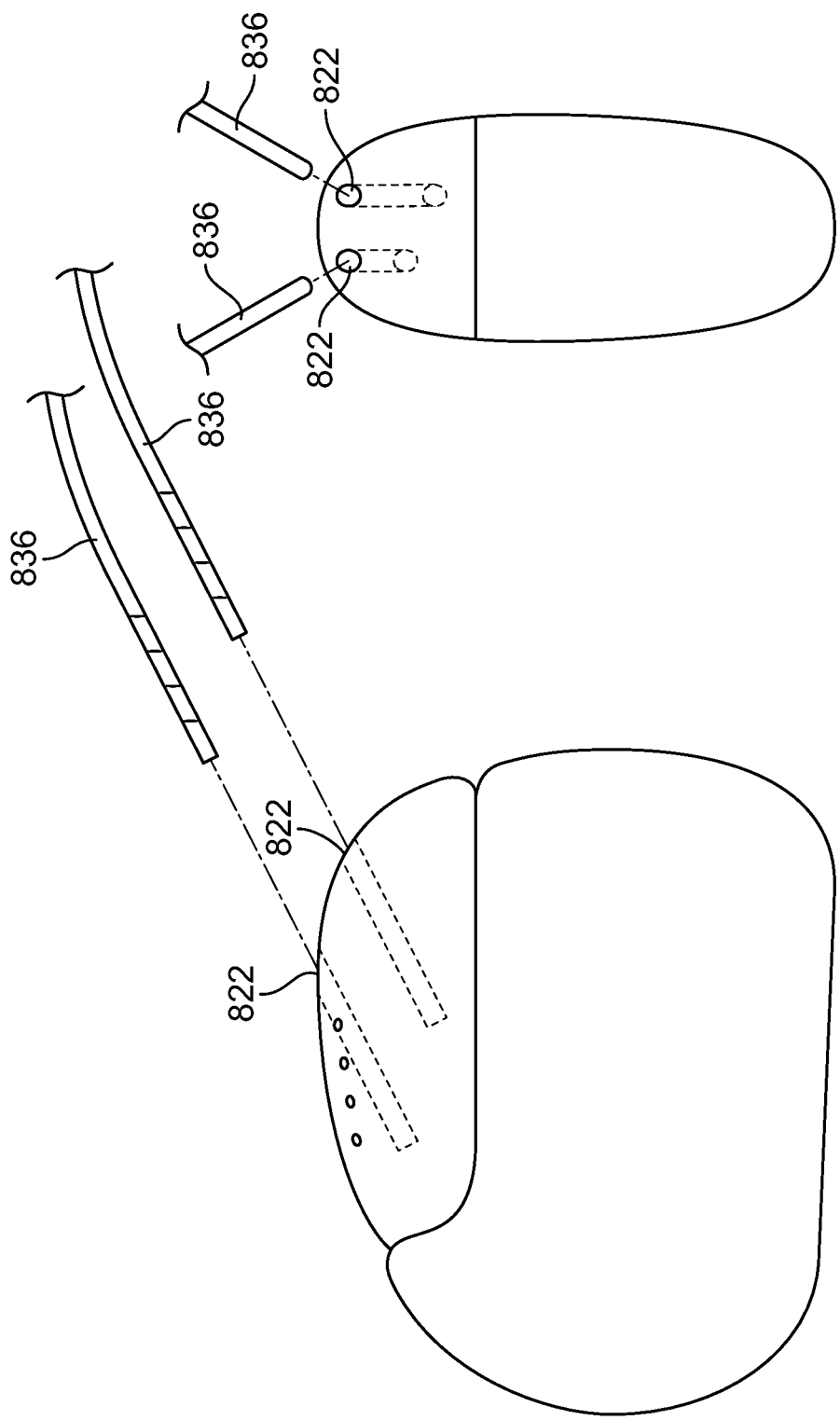
FIG. 9 is an embodiment of a neurostimulator.
Figure 10:
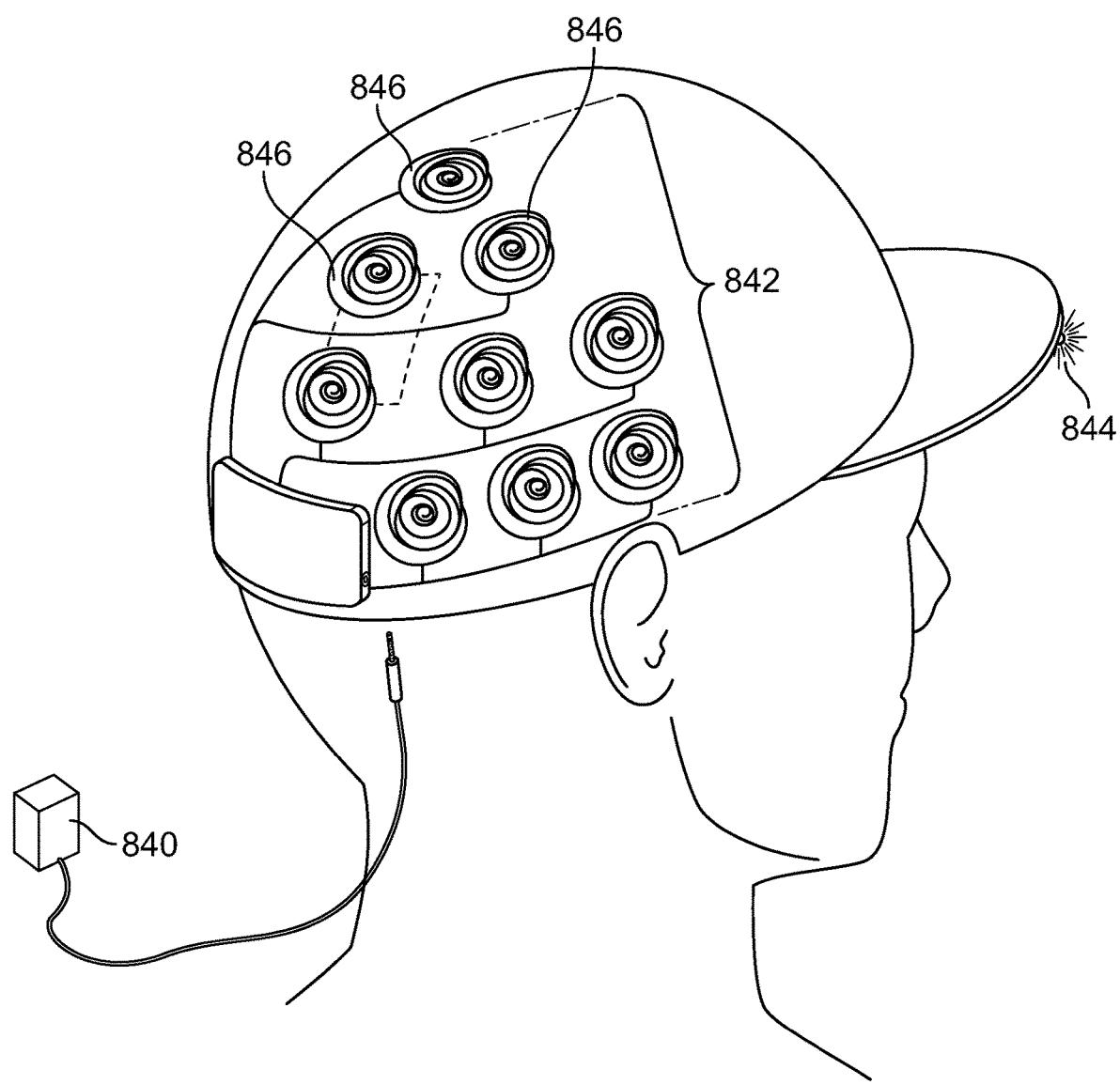
FIG. 10 is a neurostimulator with an external charger.

In a primary cell neurostimulator 810 mounted in the upper chest, the body may have a largely elliptical but asymmetrical shape. The header of the primary cell device may have two lead connector receptacles 822 that, when viewed laterally, may be staggered diagonally, with the centerline of the uppermost connector receptacle 822 and be oriented approximately 45 degrees above the lowermost connector receptacle 822, as illustrated in FIG. 9. This may allow the distance between the electrical connectors of the receptacles 822 to be maximized while minimizing the thickness of the neurostimulator. This is important for internal header construction and maintaining proper electrical separation distances, and assists in differentiating the connectors as relates to the physiologic location of the accompanying DBS lead 836.

In an embodiment, the implant may have an external charger 840. The implant charger 840 may be an external device used by the patient periodically to recharge the implanted neurostimulator 810. The charger 840 may charge the implanted neurostimulator 810 by generating a HF (High Frequency; 1 KHz-100 KHz) magnetic field over or very close to the implanted neurostimulator 810. The power recovery coil 814 of the neurostimulator 810 may convert this HF magnetic field to an AC voltage and current that may be rectified and used to power the neurostimulator 810 and recharge its secondary cell.

The charger 840 may communicate with the neurostimulator 810 using the UHF telemetry (wireless) link during the charging process. This communications link may allow the charger to know when the neurostimulator 810 is fully charged and to adjust the strength (or perhaps strength and frequency) of the HF magnetic field for optimal power coupling efficiency. This communications process may also include a failsafe mechanism that may generally prevent the maintenance of the HF magnetic field if the neurostimulator 810 is not responding or if the neurostimulator 810 has become overheated.

The charger 840 may be totally self contained and may be implemented in a cap or hat 842, as shown in FIG. 18. The normal use of the bill or brim of the cap may help the patient to correctly orient the cap on his head. Placing the cap or hat on the head may automatically turn on the charger 840 and removing it may turn the charger off. The charger may have its own rechargeable battery.

The charger in the cap/hat may have a simple indicator (LED or LCD) 844 that may notify the patient when the neurostimulator charging was competed, the status of the neurostimulator charging, the charge status of its own battery, etc.

The cap may incorporate multiple charge coils 846 that are electrically switched and/or mixed to optimally charge the implanted neurostimulator(s).

Alternatively there may be only one or two coils 846 that are electromechanically moved within the cap to optimally charge the implanted neurostimulator(s).

The charger may itself be recharged by inductive coupling when not in use. The hat or cap may be placed on a generic charging pad (such as Qi charging pads) or by placing it on a manikin or bust that includes the inductive charging coils and driving circuitry inside. Such a bust or manikin may also include an indicator that shows the status of the charger (e.g., fully charged and ready to use; or charging now, less than ½ charge currently available).

The same coils in the Charger cap/hat that generate the HF magnetic field and/or that charges the implanted neurostimulator(s) may also receive the magnetic field from the manikin/bust.

The manikin/bust may be connected to line power through a line power adapter.

C. Programmable Deep Brain Stimulation System

The system 900 may include a Clinical Programmer (CP) 910 and other additional accessories. The CP 910 may provide a mechanism for communication with the implantable Deep Brain Stimulator (DBS) 920 through the use of a wireless communication system. The CP 910 may include an electronic computing device (tablet computer, laptop, smart phone, or other electronic device) with a wireless communications subsystem, e.g., an approximately 403 MHz radio transceiver. The wireless subsystem may be physically and electronically intrinsic to the CP 910 circuitry or may be attached as a peripheral to the CP 910 (e.g. via USB). The DBS 920 stimulation settings, usage (compliance) and error logs, and other data may be transmitted to and from the CP 910 using a radio link, or any other appropriate method.

A user interface (UI) of the CP 910 may allow a clinician to choose to operate the CP 910 in several modes. These modes may include, without limitation:

A traditional or an expert mode. These modes may be similar to conventional programmers, in that voltage, frequency, and other pulse parameters are configured at a highly detailed level.

A wizard mode. The wizard mode may be a highly simplified "one knob" system (with very few controls). This UI may allow the clinician to quickly input patient parameters based on his symptom severity.

The CP 910 may allow a clinician to choose between normal pulses (regularly-spaced) or novel Deep Brain Innovations (DBI) highly effective pulses (non-regularly spaced, timing between pulses algorithmically generated). Further, the CP 910 may set the range of stimulation settings available to a clinician. It may, for example, allow the clinician to select on demand between high-efficiency or high-efficacy settings.

Figure 11:
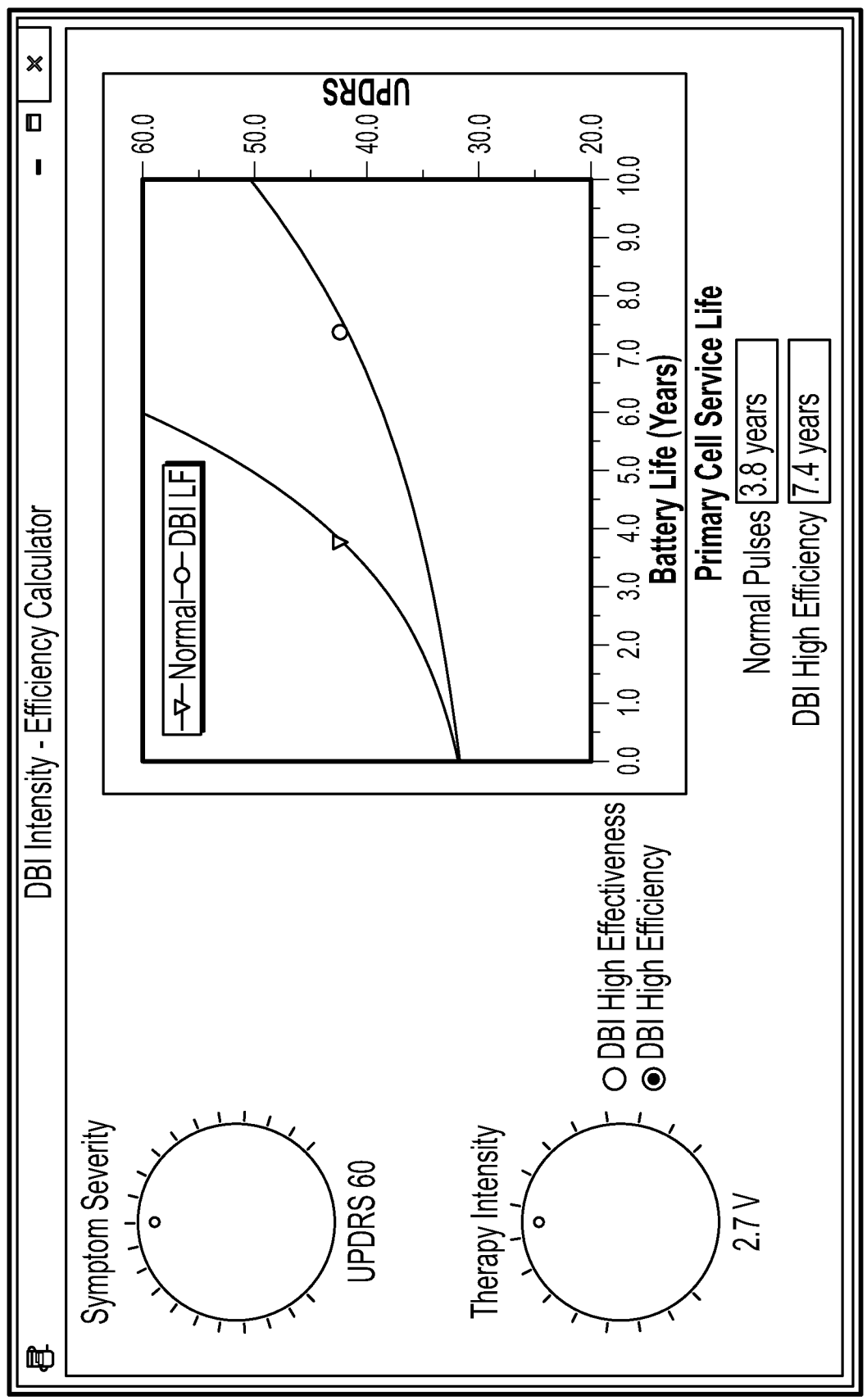
FIG. 11 is a view of a clinical programming tool that show the expected service life of an implantable neurostimulator with a normal (regular) high frequency pulse train and high efficiency deep brain innovation pulse trains according to the present teachings.
Figure 12:
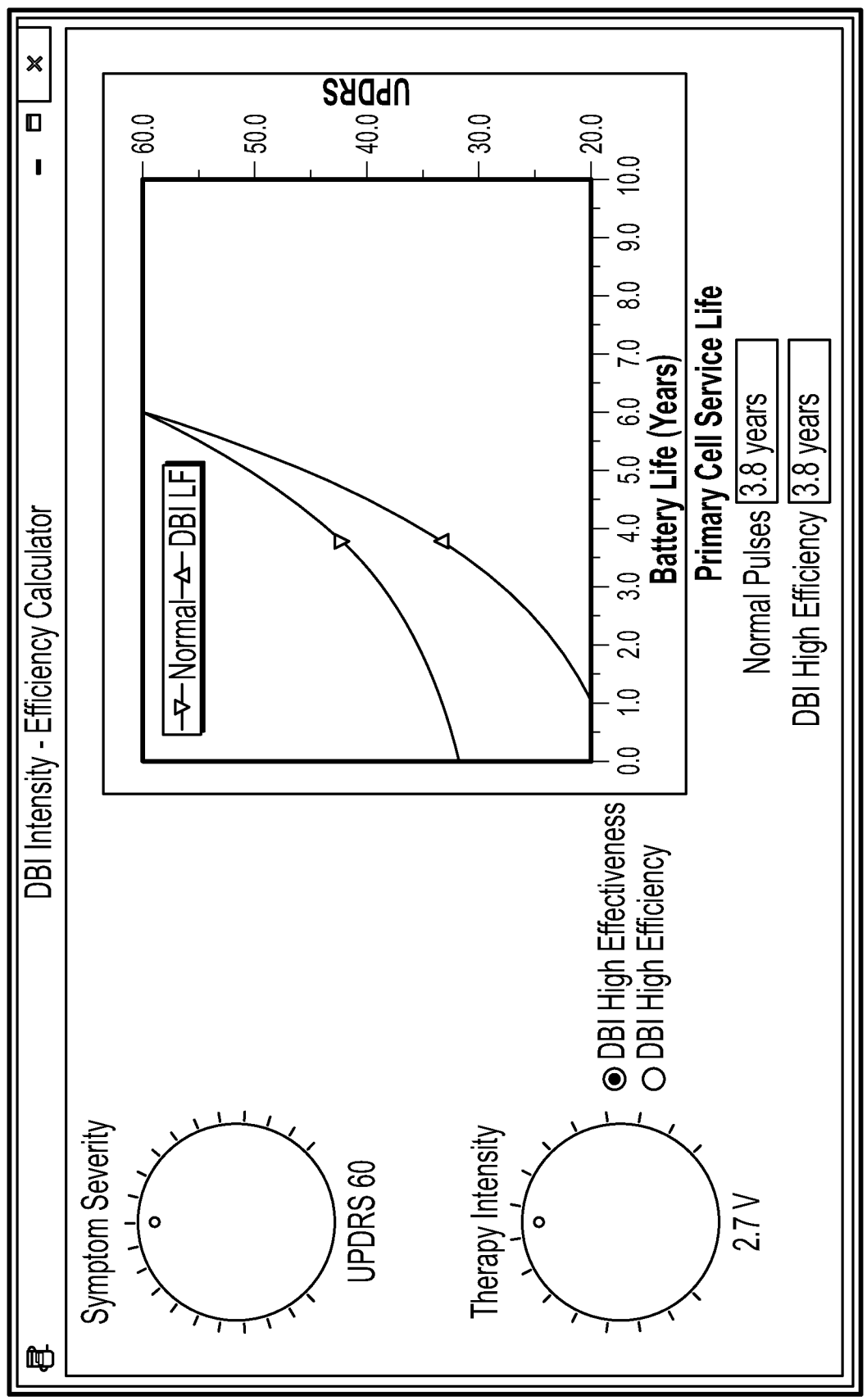
FIG. 12 is another view of the clinical programmer showing normal and high efficiency deep brain innovation pulse trains according to the present teachings.

The CP 910 may include a feature that allows the clinician to choose a balance of stimulation parameters that trade off battery efficiency (battery service life or recharge interval) and stimulation effectiveness. As shown in FIGS. 11 and 12, using a simple graphical user interface, the clinician may "dial up" different levels of stimulation and quickly see the estimated battery life and efficacy. The tradeoff calculation may include the comparison of normal pulses, low-frequency efficient novel DBI pulse trains, or high-frequency high efficacy novel DBI pulse trains.

Figure 13:
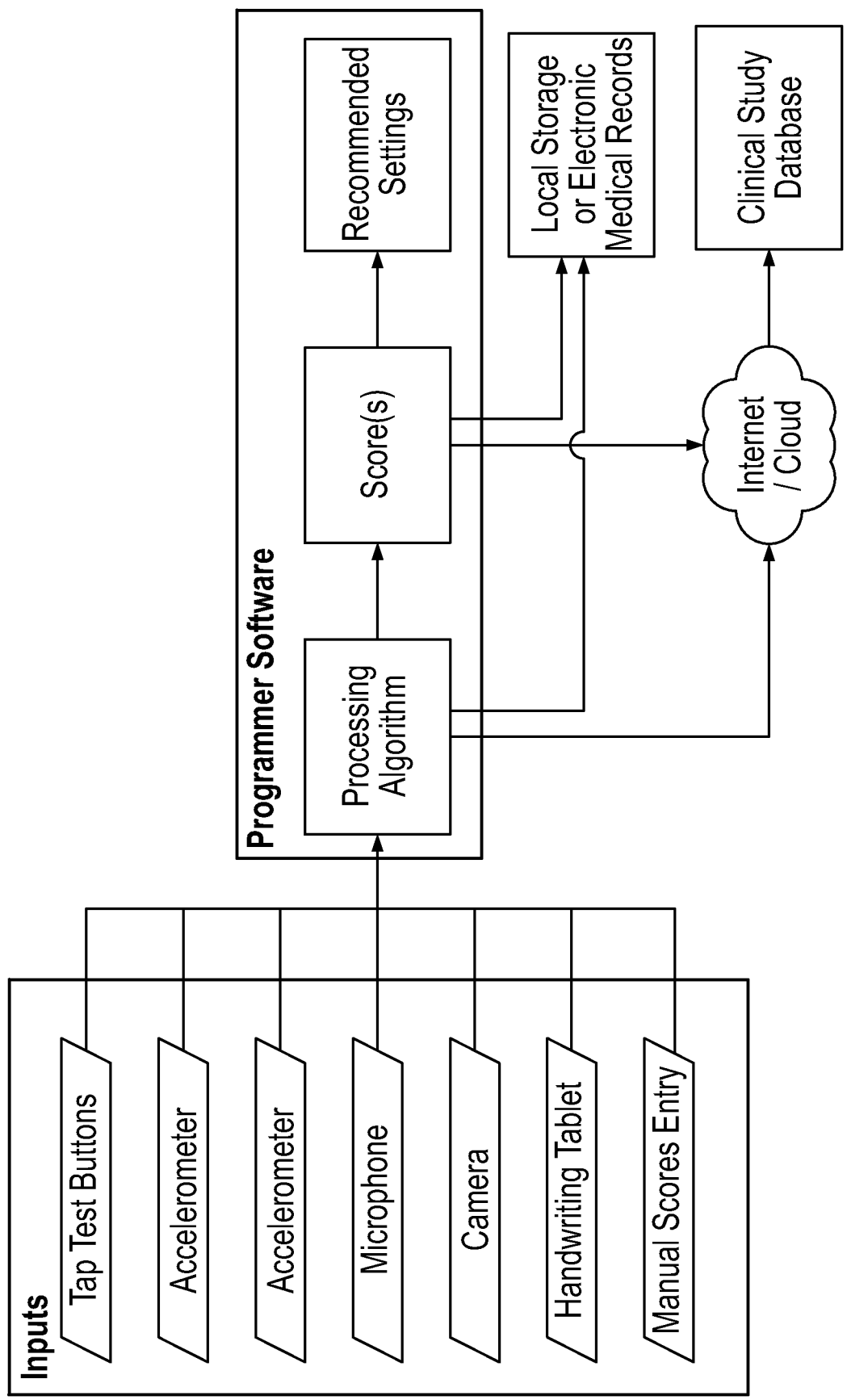
FIG. 13 is a view of programmer inputs and processing flow according to the present teachings.

As shown in FIG. 13, the CP 910 may include a compatibility mode that allows the clinician to electronically import or manually enter stimulation settings from a previously implanted DBS system 900. The imported settings may generate any appropriate or required pulses. Additionally, the CP 910 may incorporate a variety of sensors and user inputs that may be assimilated to assess treatment effectiveness and guide the clinician in programming parameters. Inclusion of the inputs into the programming environment may facilitate consistent, quantitative analysis of patient symptoms. Data may be collected quickly before, during, and after programming. Sensors and inputs may include:

A mouse or buttons to perform a "tap test." The mouse or buttons may measure speed and/or consistency of alternating finger taps.

An accelerometer. This accelerometer may be hand held, wrist mounted, or otherwise held by the patient. The accelerometer may quantify tremors.

A microphone. By speaking or making other noises, a microphone may capture the patient's sounds and analyze them for symptoms.

A camera. A camera may record videos of patients performing activities such as walking, raising their arms, pinching their fingers, etc. The videos may be processed into a quantitative result indicating symptom severity, or simply recorded for qualitative analysis by clinicians. The camera may be 3D or depth-perceiving (RGB-D, Kinect).

A handwriting tablet. The handwriting tablet may allow for the quality of patients' handwriting, such as their signature, to be analyzed.

A manual clinician scoring. A clinician may manually score the patient, e.g., conventional scores may be entered, such as all or partial Unified Parkinson's Diagnosis Rating Score (UPDRS).

A still or video camera. The camera may be used to take images or videos before, during, and/or after programming to record the state of the patient's symptoms. The image(s) may be overlaid with the stimulator settings at the time the photo/video was taken for a comparison.

Figure 14:
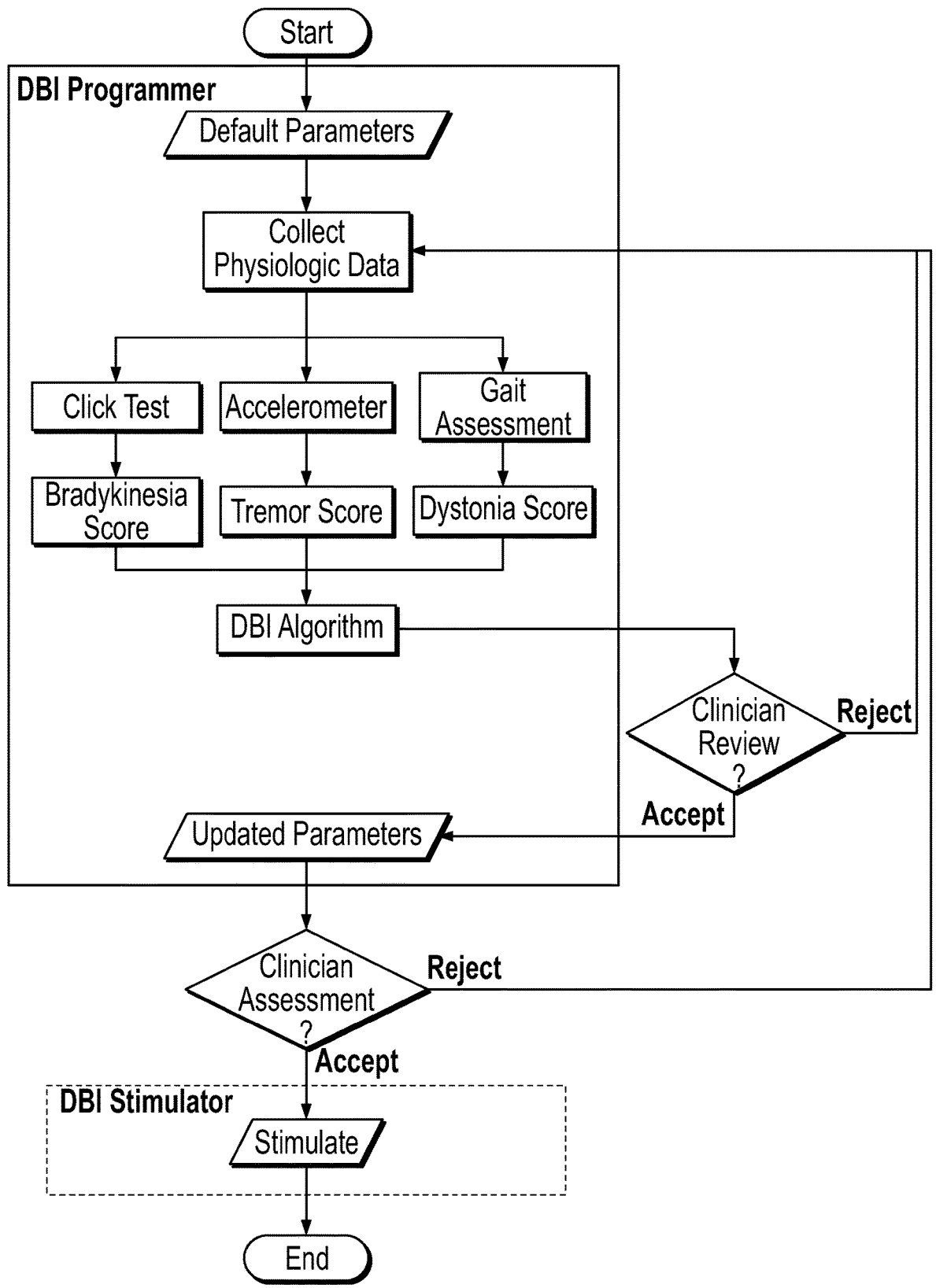
FIG. 14 is another view of a programmer inputs and processing flow according to the present teachings.

As shown in FIG. 14, the inputs may be used to aid in a guided, closed loop programming session where settings may be made, symptoms may be assessed, and settings may be iteratively adjusted. By way of a non-limiting example, the clinician may apply a first stimulation to the patient. The first stimulation may be based upon default parameters, i.e., it may include a non-regular pulse train that typically provides adequate efficiency (i.e., battery life), efficacy, and/or reduction of side effects. The clinician may collect certain physiologic data on the patient using any one of the tests identified above. Based upon the outcome of this evaluation, the clinician may utilize the CP 910 to modify the stimulation pattern. The modified stimulation pattern to be applied may be based upon an evaluation of characteristics of the electrical stimulation, such as non-regular pulse trains, through use, for example of a global optimization algorithm (including, without limitation a genetic algorithm). The clinician may use the CP 910 to modify the stimulation pattern to match the identified non-regular pulse train. The clinician may them re-evaluate the patient as described above. These steps may be repeated and a different non-regular pulse train may be applied until the desired efficacy, efficiency and reduction of side effects is reached.

The CP 910 may improve the flow of interaction with the clinician. For example, the CP 910 may be programmed such that the CP 910 is easier for a clinician to use and provides a more natural and intuitive system. The CP 910 may be programmed to be easy for the clinician to alter the parameters of application of electrical stimulation. Clearly identifiable adjustment controls may be provided as well as clearly shown information regarding the stimulation parameters being applied.

By way of a non-limiting example, the CP 910 may include a plurality of programming sequences programmed therein. An exemplary programming sequence may include selecting stimulus electrodes and current distributions among the stimulus electrodes with a stimulus amplitude, applying a first non-regular pulse train designed for efficient operation of the stimulator, refining a stimulus amplitude to achieve symptom reduction while minimizing side effects, and selecting a second non-regular pulse train designed for greater symptom reduction at a cost of a shorter operating life for the DBS 920.

Figure 15:
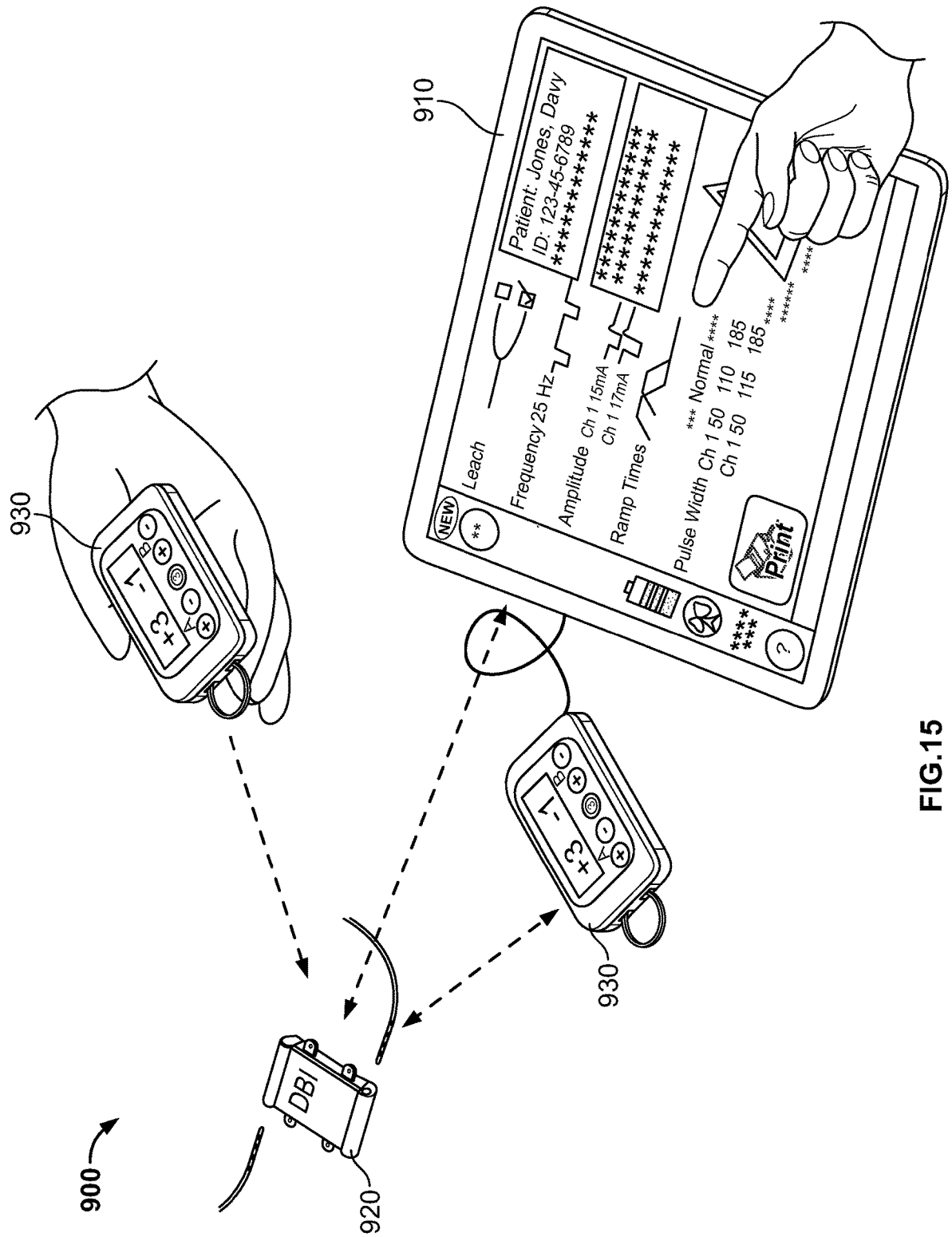
FIG. 15 is a view of a patient remote and programmer with the wireless telemetry module according to the present teachings.

As shown in FIG. 15, the system may have a Patient Remote Controller 930 ("Remote"). The Remote 930 may allow the patient limited control over his DBS 920, e.g., including turning stimulation on and off, and adjusting the settings within a limited range, such as high-efficiency and high-efficacy. Like the CP, the Remote 930 may use a wireless link to communicate with the DBS 920. The Remote 930 may have a touch-screen display that offers a dynamic, flexible user interface that changes based on the context of usage. The display may be "e-ink" for very low power consumption and high readability. The Remote 930 may further include some of the same sensors as the CP, including, without limitation accelerometers. The sensors may be used to record and assess patient symptoms at various times, but not necessarily in a clinical setting.

To prevent accidental button presses, particularly if used with a touch screen, the Remote 930 may incorporate a capacitive touch or other sensor to ensure that the Remote 930 is being held in a hand before button presses are permitted.

Because of the similarity of the radio electronics in the Remote 930 and the wireless subsystem of the CP 910, the Remote 930 may act as the wireless subsystem when attached to a CP 910. Using this mechanism, the programmer 910 may configure the Remote 930 to work with a particular patient's DBS 920. There is also no need for the independent development of a wireless telemetry module for the CP 910 alone. The Remote 930 may be connected to the programmer 910 via USB.

The Remote 930 may be configured to allow the patient to modify the DBS 920, or more specifically the neurostimulator applying the electrical stimulation to the patient. The DBS 920 may be programmed, such as by the clinician, to provide alternative treatments for the patient to choose between. For example, the Remote 930 may allow a patient to select the stimulus patterns and parameters programmed by the clinician to offer patients the option of temporarily selecting a stimulation that has increased effectiveness at reducing the primary symptoms of their disease or condition even if that choice results in reduced operating life or increases in side effects of the stimulation. This on the spot patient choice of this treatment/side effects tradeoff may allow the patient to optimize his/her treatment for his/her personal needs and circumstances. In these embodiments, the patient may need to go out in public and may want to increase or ramp up the efficacy of the treatment. The patient may be able to use the Remote 930 and change from a first temporal non-regular pattern to a second temporal non-regular pattern that may increase efficacy and/or efficiency. In addition, the patient may be able to use the Remote 930 and change from a first temporal regular pattern to a second temporal regular pattern that may increase efficacy and/or efficiency.

However, the Remote 930 may only allow the patient to select from a small number of stimulus patterns (or stimulus parameter sets) that have been programmed by the clinician (such as through the CP 910). Thus the clinician may program each pattern (or stimulus set) to be safe and have a special benefit to the patient. The Remote 930, for example, may limit the selection of the DBS 920 to go from a standard setting to an increased efficacy setting. Increasing the efficacy may reduce the degree of tremor or spasticity of the patient. The present teachings are not limited to the DBS 920 and Remote 930 settings disclosed herein. Any appropriate settings may be programmed into the Remote 930.

The present teachings may be combined to provide an efficient and effective system to apply neurostimulation to a patient. By way of a non-limiting example, the rechargeable neurostimulator 810 may be utilized with a patient so as to treat a neurological condition or symptoms of such patent. The rechargeable neurostimulator 810 may be implanted into the patient as described above. The lead further described above, may be operatively coupled with the rechargeable neurostimulator 810 in any appropriate manner. The lead may be configured to include at least one electrode to apply electrical stimulation to the patient. The rechargeable neurostimulator 810 may be operatively coupled with the CP 910, such as being wirelessly coupled. The CP 910 may be utilized to program or otherwise alter the rechargeable neurostimulator 810 so as to apply a predetermined stimulation through the lead to the patient. The CP 910 may be utilized to fine tune the stimulation or otherwise alter the stimulation being applied.

By way of a non-limiting example, in operation the user, such as a clinician, may utilize the CP 910 to alter the stimulation parameters being applied so as to improve the efficiency and/or efficacy of the treatment. The stimulation may consist of a non-regular pulse train that includes a plurality of single pulses and embedded multiple pulse groups with non-regular, non-random, differing inter-pulse intervals between the single pulses and non-regular inter-pulse intervals within the embedded multiple pulse groups. The stimulation may repeat these pulse trains to treat the neurological condition of the patient, which may include, without limitation, Parkinson's Disease, Essential Tremor, Movement Disorders, Dystonia, Epilepsy, Pain, psychiatric disorders such as Obsessive Compulsive Disorder, Depression, and Tourette's Syndrome among others.

The clinician may evaluate the patient and/or rechargeable neurostimulator 810. If the symptoms are not sufficiently controlled, the battery life is not at a predetermined level, the side effects are too great, or any combination of such, the clinician may utilize the CP 910 to alter the stimulation parameters, including, without limitation that non-regular pulse train, the regular pulse train, or the waveform shapes or a combination of such. Either or both of the rechargeable neurostimulator 810 of the CP 910 may include a plurality of such non-regular pulse trains (or regular pulse trains as applicable) that may be applied so as to improve any one of the battery life, efficacy and reduction of side effects. In such embodiments, the clinician may continue to apply these predetermined pulse trains until the appropriate one is applied. It should be understood that in the embodiment in which the CP 910 solely contains the applicable pulse trains, it may transmit a signal, such as wirelessly, to the rechargeable neurostimulator 810 to reprogram such to apply such applicable pulse trains. The CP 910 may also be capable of receiving additional electrical stimulation parameter(s), including, without limitation non-regular stimulus patterns, regular stimulus patterns, waveform shape, etc. from other sources (e.g., from the manufacturer of the CP or the neurostimulator). These new stimulation parameters may be added to the CP910 via an internet connection or a mass storage device such as a USB memory device. These new stimulation parameters may be downloaded to the neurostimulator via the wireless (UHF) link between the CP 910 and the neurostimulator.

Although the embodiments of the present invention have been illustrated in the accompanying drawings and described in the foregoing detailed description, it is to be understood that the present invention is not to be limited to just the embodiments disclosed, but that the invention described herein is capable of numerous rearrangements, modifications and substitutions without departing from the scope of the claims hereafter. The claims as follows are intended to include all modifications and alterations insofar as they come within the scope of the claims or the equivalent thereof.

What is claimed is:

1. A neurostimulation system comprising:
   a deep brain stimulator configured to be implanted in a cranium of a body in operable communication with a patient's nervous system, the stimulator configured to (i) generate an electrical signal and (ii) apply a non-regular, non-random, differing pulse stimulation pattern, wherein the deep brain stimulator comprises:
      a cylindrical body configured to fit within a cranial bore and a tab, eyelet, wing or flange extending from the body and wherein the tab, eyelet, wing or flange are configured to be secured to the cranium; and
      a stimulator telemetry component positioned in the cylindrical body;
   an electrode extending from the cylindrical body;
   a clinical programmer comprising a programmer telemetry component operatively and wirelessly coupled with the stimulator telemetry component, wherein the clinical programmer controls application of the pulse stimulation pattern by modifying at least one characteristic of the pulse stimulation pattern to improve the efficacy of the pulse stimulation pattern;

wherein the stimulator includes a battery having a life span and wherein an input provided by an interface on the clinical programmer enables modifying the at least one characteristic of the pulse stimulation pattern to increase the life span of the battery, and wherein a power recovery coil is in operative communication with the deep brain stimulator;

an external charger positioned in a hat configured to be placed on a head of a patient, wherein the external charger is capable of wirelessly charging the battery via the power recovery coil, wherein communication between the external charger and the deep brain electrical stimulator comprises a failsafe mechanism preventing charging between the external charger and the power recovery coil if the deep brain electrical stimulator is non-operative; and a handheld patient remote controller operatively and wirelessly coupled with the deep brain stimulator.

2. The neurostimulation system of claim 1, wherein the clinical programmer operates in combination with a wireless communications subsystem.

3. The neurostimulation system of claim 1, wherein the clinical programmer further comprises sensors to collect data.

4. The neurostimulation system of claim 1, wherein the remote control comprises a capacitive touch sensor configured to prevent operation of the remote control unless the remote control is positioned in a hand of a user.

5. The neurostimulation system of claim 1, wherein the deep brain stimulator receives a plurality of electrical signals from a memory unit associated with the clinical programmer.

6. The neurostimulation system of claim 1, wherein the deep brain stimulator receives the plurality of non-regular pulse timing from a memory unit associated with the clinical programmer.

7. The neurostimulation system of claim 6, wherein the remote controller is configured to allow a patient to select a first non-regular pulse timing from the plurality of non-regular pulse timing.

8. The neurostimulation system of claim 7, wherein the first non-regular pulse timing relates to a predefined benefit.

9. The neurostimulation system of claim 8, wherein the first non-regular pulse timing changes to a second non-regular pulse timing of the plurality of non-regular pulse timing after a period of time.

10. The neurostimulation system of claim 1, wherein the at least one characteristic of the pulse stimulation pattern incudes a plurality of characteristics of the pulse stimulation pattern and whereby the remote controller is in operative communication with the deep brain stimulator to allow a patient to modify a first characteristic of the pulse stimulation pattern from the plurality of characteristics of the pulse stimulation pattern.

11. The neurostimulation system of claim 10, wherein the remote controller communicates with the stimulator using a wireless communications link.

12. The neurostimulation system of claim 1, wherein the clinical programmer prompts a clinician to program the stimulator in a predetermined order.

13. The neurostimulation system of claim 12, wherein the prompting of the clinician is provided by changing screen images.

14. The neurostimulation system of claim 12, wherein the prompting of the clinician is provided by a programming status bar.

15. The neurostimulation system of claim 1, wherein the clinical programmer includes a plurality of programming sequences, whereby one of the plurality of programming sequences is a default programming sequence.

16. The neurostimulation system of claim 15, wherein the default programming sequence is changed to another of the plurality of programming sequences.

17. The neurostimulation system of claim 15, wherein the clinical programmer reports a status as tasks are completed during programming the clinical programmer.

18. The neurostimulation system of claim 1, wherein pulse stimulation pattern is programmed into the stimulator by a wireless communications link from the clinical programmer.

19. The neurostimulation system of claim 18, wherein pulse stimulation pattern is selected or adjusted by a clinician using the clinical programmer.

20. A neurostimulation system comprising:

a deep brain stimulator configured to be implanted in a cranium of a body in communication with a patient's nervous system said stimulator configured to generate an electrical signal, wherein the deep brain stimulator comprises: (i) cylindrical body configured to fit within a cranial bore and a tab, eyelet, wing or flange extending from the body and wherein the tab, eyelet, wing or flange are configured to be secured to a cranium and (ii) a stimulator telemetry component positioned in the cylindrical body;

a clinical programmer operatively and wirelessly coupled with the deep brain stimulator, said clinical programmer comprising: (i) a programmer telemetry component programmed to control the electrical signal of the stimulator by modifying at least one characteristic of the electrical signal to reduce power consumption while delivering a pulse train, wherein the pulse train includes a plurality of single pulses and embedded multiple pulse groups, with non-regular, non-random, differing inter-pulse intervals between the single pulses and the embedded multiple pulse groups, and (ii) a graphical user interface to display a comparative analysis of the modified electrical signal and wherein, over time, the modified electrical signal maintains a similar level or greater level of effectiveness at activating neural structure, and wherein a power recovery coil is in operative communication with the deep brain stimulator;

an external charger positioned in a hat configured to be placed on a head of a patient, wherein the external charger is capable of wirelessly charging the battery via the power recovery coil, wherein communication between the external charger and the deep brain electrical stimulator comprises a failsafe mechanism preventing charging between the external charger and the power recovery coil if the deep brain electrical stimulator is non-operative; and a handheld remote controller operatively and wirelessly coupled with the deep brain stimulator.

21. The neurostimulation system of claim 20, wherein modifying the at least one characteristic includes modifying at least characteristic of the pulse train.

22. The neurostimulation system of claim 20, wherein the pulse train includes a repeating sequence of the pulse train.

23. The neurostimulation system of claim 22, wherein modifying the at least one characteristic includes modifying the repeating sequence of the pulse train.

24. A neurostimulation system for treating a neurological condition, the neurostimulation system comprising:
- a deep brain electrical stimulator configured to be implanted in a cranium of a body and configured to generate a first stimulus pattern, wherein the deep brain electrical stimulator comprises: (i) a cylindrical body configured to fit within a cranial bore and a tab, eyelet, wing or flange extending from the body and wherein the tab, eyelet, wing or flange are configured to be secured to a cranium, and (ii) a stimulator telemetry component positioned in the cylindrical body;
- a power source coupled with the deep brain electrical stimulator;
- a power recovery coil in operative communication with the deep brain stimulator;
- an electrode coupled with the deep brain electrical stimulator;
- a programmer operatively coupled with the deep brain electrical stimulator, wherein the programmer has a programmer telemetry component and an input interface, said programmer telemetry component communicates with the electrical stimulator to apply a second stimulus pattern, wherein the second stimulus pattern has increased effectiveness at reducing the neurological condition and said input interface displaying comparative information to solicit input for improving an operating life of the power source,
- wherein at least one of the first or second stimulus pattern includes a non-regular, non-random, differing pulse pattern;
- an external charger positioned in a hat configured to be placed on a head of a patient, wherein the external charger is capable of wirelessly charging the battery via the power recovery coil and wherein communication between the external charger and the deep brain electrical stimulator comprises a failsafe mechanism preventing charging between the external charger and the power recovery coil if the deep brain electrical stimulator is non-operative; and
- a handheld remote controller operatively and wirelessly coupled with the deep brain electrical stimulator.

25. The neurostimulation system of claim 24, wherein the second stimulus pattern decreases side effects.

* * * * *